(12) United States Patent
Flavell et al.

(10) Patent No.: US 6,716,591 B1
(45) Date of Patent: Apr. 6, 2004

(54) B. BURGDORFERI POLYPEPTIDES

(75) Inventors: Richard A. Flavell, Killingworth, CT (US); Erol Fikrig, Guilford, CT (US); Tuan T. Lam, San Jose, CA (US); Fred S. Kantor, Orange, CT (US); Stephen W. Barthold, Madison, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/152,588

(22) Filed: Sep. 14, 1998

Related U.S. Application Data

(60) Division of application No. 08/909,119, filed on Aug. 11, 1997, now Pat. No. 5,807,685, which is a division of application No. 08/118,469, filed on Sep. 8, 1993, now Pat. No. 5,656,451, which is a continuation-in-part of application No. 08/099,757, filed on Jul. 30, 1993, now abandoned.

(51) Int. Cl.[7] .............................................. G01N 33/53
(52) U.S. Cl. .................... 435/7.22; 435/7.1; 435/7.2; 530/350; 530/387.1; 530/389.1
(58) Field of Search ........................ 530/387.1, 387.9, 530/388.1, 388.4, 389.1, 389.5, 388.82, 300, 350; 435/4, 7.1, 7.2, 7.22, 7.32, 34, 975

(56) References Cited

U.S. PATENT DOCUMENTS

| | | |
|---|---|---|
| 4,721,617 A | 1/1988 | Johnson |
| 4,772,464 A | 9/1988 | Rutherford et al. |
| 5,178,859 A | 1/1993 | Simon et al. |
| 5,217,872 A | 6/1993 | Dorward et al. |
| 5,403,718 A * | 4/1995 | Dorward et al. |

FOREIGN PATENT DOCUMENTS

| | | |
|---|---|---|
| CA | 2025597 | 3/1991 |
| WO | WO 90/02564 * | 3/1990 |
| WO | WO 90/04411 | 5/1990 |
| WO | WO 91/09870 | 7/1991 |
| WO | WO 93/00448 | 1/1993 |
| WO | WO 93/08286 | 4/1993 |
| WO | WO 93/08306 | 4/1993 |
| WO | WO 93/10237 | 5/1993 |

OTHER PUBLICATIONS

Kramer, M. D. et al., Characterization of *Borrelia burgdorferi* associated antigens by monoclonal antibodies. Immunobiol., 181: 357–366, 1990.*

Wallich, R. et al., Molecular and immunological characterization of a novel polymorphic lipoprotein of *borrelia burgdorferi*. Infection and Immunity. 61: 4158–4166, Oct. 1993.*

Akins et al., Molecular Microbiology 18:507–520, 1995.*

Lin et al., Biochemistry 14:1599, 1975.*

Schwartz et al., Proc. Natl. Acad. Sci. USA 84:6408–6411, 1987.*

Burgess et al., The Journal of Cell Biology 111:2129–2138, 1990.*

Lazar et al., Molecular and Cellular Biology 8:1247–1252, 1988.*

Rieger et al., Glossary of Genetics and Cytogenetics, Springer–Verlag, NY, pp. 17–18, 1976.*

A.G. Barbour, et al., "Heterogeneity of Major Proteins in Lyme Disease Borreliae: A Molecular Analysis of North American and European Isolates", *J. Infect. Dis.*, 152, pp. 478–484 (1985).

G. Beck, et al., "Chemical and Biologic Characterization of a Lipopolysaccharide Extracted From the Lyme Disease Sprirochete (*Borrelia burgdorferi*)", *J. Infect. Dis.*, 152, pp. 108–117 (1985).

M. Brandt et al., "Immunogenic Integral Membrane Proteins of *Borrelia burgdorferi* Are Lipoproteins", *Infect. Immun.*, 58, pp. 983–991 (1990).

J.L. Coleman and J.L. Benach, "Isolation of Antigenic Components from the Lyme Disease Spirochete: Their Role in Early Diagnosis", *J. Infect. Dis.*, 155, pp. 756–765 (1987).

J.E. Craft et al., "Antigens of *Borrelia burgdorferi* Recognized during Lyme Disease", *J. Clin. Invest.*, 78, pp. 934–936 (1986).

M.S. deSouza, et al., "Long–Term Study of Cell–Mediated Responses to *Borrelia burgdorferi* in the Laboratory Mouse", *Infect. Immun.*, 61, pp. 1814–1822.

EMBL Database, entry BBLA7 Accession No. X70826; Feb. 8, 1993.

L.F. Erdile, et al., "Role of Attached Lipid in Immunogenicity of *BOrrelia burgdorferi* OspA", *Infect. Immun.*, 61, pp. 81–90 (1993).

E. Fikrig et al., "Protection of Mice Against the Lyme Disease Agent by Immunizing with Recombinant OspA", *Science*, 250, pp. 553–556 (1990).

E. Fikrig et al., "Elimination of *Borrelia burgdorferi* From Vector Ticks Feeding on OspA–Immunized Mice", *Proc. Natl. Acad. Sci. USA*, 89, pp. 5418–5421 (1992).

F. Fuchs et al., "Molecular Analysis and Expression of a *Borrelia burgdorferi* gene encoding a 22kDa protein (pC) in *Escherichia coli*", *Mol. Micro.*, 6, pp. 503–509 (1992).

(List continued on next page.)

Primary Examiner—Larry R. Helms
(74) Attorney, Agent, or Firm—Fish & Neave; James F. Haley, Jr.; Andrew K. Holmes

(57) ABSTRACT

Methods and compositions for the prevention, treatment and diagnosis of Lyme disease. Novel *B. burgdorferi* polypeptides, serotypic variants thereof, fragments thereof and derivatives thereof. Fusion proteins and multimeric proteins comprising same. Multicomponent vaccines comprising novel *B. burgdorferi* polypeptides in addition to other immunogenic *B. burgdorferi* polypeptides. DNA sequences, recombinant DNA molecules and transformed host cells useful in the compositions and methods. Antibodies directed against the novel *B. burgdorferi* polypeptides, and diagnostic kits comprising the polypeptides or antibodies.

7 Claims, 16 Drawing Sheets-

OTHER PUBLICATIONS

R.L. Grodzicki and A.C. Steers, "Comparison of Immunoblotting and Indirect Enzyme–Linked Immunosorbent Assay Using Different Antigen Preparations for Diagnosing Early Lyme Disease", *J. Infect. Dis.*, 157, pp. 790–797, (1988).

T.R. Howe et al., "A Single Recombinant Plasmid Expressing Two Major Outer Surface Proteins of the Lyme Disease Spirochete", *Science*, 227, pp. 645–646 (1985).

W. Jiang et al., "Cross–Antigenicity Between The Major Surface Proteins (OspA and OspB) And Other Proteins Of *Borrelia burgdorferi*", *J. Immunol.*, 144, pp. 284–289 (1990).

R.C. Johnson et al., "Active Immunization of Hamsters against Experimental Infection with *Borrelia burgdorferi*", *Infect. Immun.*, 54, pp. 897–898 (1986).

R.C. Johnson, et al., "Passive Immunization of Hamsters against Experimental Infection with the Lyme Disease Spirochete", *Infect. Immun.*, 53, pp. 713–714 (1986).

M.D. Kramer, et al., "Die Borrelia–burgdorferi–Infektion", *Ubersichten*, 41, pp. 648–657 (1990).

M.D. Kramer, et al., "Characterization of *Borrelia burgdorferi* Associated Antigens by Monoclonal Antibodies", *Immunobiol.*, 181, pp. 357–366 (1990).

R.S. Lane and J.A. Pascocello, "Antigenic Characteristics of *Borrelia burgdorferi* Isolates from Ixodid Ticks in California," *J. Clin. Microbiol.*, 27, pp. 2344–2349 (1989).

R. B. LeFebvre, et al., "Characterization of *Borrelia burgdorferi* Isolates by Restriction Endonuclease Analysis and DNA Hybridization", *J. Clin. Microbiol.*, 27, pp. 636–639 (1989).

B. J. Luft et al., "Biochemical and Immunological Characterization of the Surface Proteins of *Borrelia burgdorferi*", *Infect. Immun.*, 57, pp. 3637–3645 (1989).

L.A. Magnarelli, et al., "Cross–Reactivity in Serological Tests for Lyme Disease and Other Spirochetal Infections", *J. Infect. Dis.*, 156, pp. 183–188 (1987).

S.J. Norris et al., Low–Passage–Associated Proteins of *Borrelia burgdorferi* B31: Characterization and Molecular Cloning of OspD, a Surface–Exposed, Plasmid–Encoded Lipoprotein, *Infect. Immun.*, 60, pp. 4662–4672 (1992).

V. Preac–Mursic, et al., "Active Immunization with pC Protein of *Borrelia burgdorferi* Protects Gerbils against *B. burgdorferi* Infection", *Infection*, 20, pp. 342–348 (1992).

A. Sadziene, et al., "Antibody–resistant Mutants of *Borrelia burgdorferi*: In Vitro Selection and Characterization", *J. Exper. Med.*, 176, pp. 799–809.

U.E. Schaible, et al., "Monoclonal antibodies specific for the outer surface protein A (OspA) of *Borrelia burgdorferi* prevent Lyme borreliosis in severe combined immunodeficiency (scid) mice", *Proc. Natl. Acad. Sci. USA*, 87, pp. 3768–3772 (1990).

U.E. Schaible, et al., "A Mouse Model for *Borrelia burgdorferi* Infection: Pathogenesis, Immune Response and Protection", *Behring Inst. Mitt.*, 88, pp. 59–67 (1991).

U.E. Schaible, et al., "Demonstration of Antigen–Specific T Cells and Histopathological Alterations in Mice Experimentally Inoculated with *Borrelia burgdorferi*", *Infect. Immun.*, 57, pp. 41–47 (1989).

J.L. Schmitz, et al., "Passive Immunication Prevents Induction of Lyme Arthritis in LSH Hamsters", *Infect. Immun.*, 58, pp. 144–148 (1990).

T.G. Schwan et al., "Changes in Infectivity and Plasmid Profile of the Lyme Disease Spirochete, *Borrelia burgdorferi*, as a Result of In Vitro Cultivation", *Infect. Immun.*, 56, pp. 1831–1836 (1988).

J.E. Sears, et al., "Molecular Mapping Of Osp–A Mediated Immunity Against *Borrelia burgdorferi*, The Agent of Lyme Disease", *J. Immunol.*, 147, pp. 1995–2000 (1991).

M.M. Simon, et al., "A Mouse Model for *Borrelia burgdorferi* Infection: Approach To A Vaccine Against Lyme Disease," *Immunol. Today*, 12, pp. 11–16 (1991).

W.J. Simpson et al., "Reactivity of Human Lyme Borreliosis Sera with a 39–Kilodation Antigen Specific to *Borrelia burgdorferi*", *J. Clin. Microbiol.*, 28, pp. 1329–1337 (1990).

D.J. Volkman et al., "Characterization Of An Immunoreactive 93–k–Da Core Protein Of *Borrelia burgdorferi* With A Human IgG Monoclonal Antibody", *J. Immunol.*, 146, pp. 3177–3182 (1991).

T.A. Waldmann, "Monoclonal Antibodies in Diagnosis and Therapy", *Science*, 252, pp. 1657–1662 (1991).

R. Wallich et al., "The *Borrelia burgdorferi* Flagellum–Associated 41–Kilodation Antigen (Flagellin): Molecular Cloning, Expression, and Amplification of the Gene", *Infect. Immun.*, 58, pp. 7111–1719 (1990).

B. Wilske, et al., "Antigenic Variability of *Borrelia burgdorferi*", *Annals of N.Y. Acad. of Sciences*, pp. 126–143.

B. Wilske et al., "Immunochemical Analysis of the Immune Response in Late Manifestations of Lyme Borreliosis", *Zbl. Bakt. Hyg.*, 267, pp. 549–559 (1988).

B. Wilske, et al., "Immunochemical and Immunological Analysis of European *Borrelia burgdorferi* Strains", *Zbl. Bakt. Hyg.*, 263, pp. 92–102 (1986). Abstract Only.

* cited by examiner

| Consensus | "-35 region" TTGACA | "-10 region" TATAAT | Ribosomal binding site AAAGGAGGTGATC |
|---|---|---|---|
| Osp A | TTGTTA | TATAAT | AAAGGAG |
| Osp B | | | AAGGAG |
| Osp C | TTGAAA | TATAAA | AAAGGAGG |
| Osp D | TTGATA | TATAAT | AAGGAG |
| Osp E | TTGTTA | TATATT | GGAG |
| Osp F | | | AGGAG |

FIG. 2

|  | OspE (%) | OspF (%) |
|---|---|---|
| Alanine (A) | 6 (3.51) | 11 (4.78) |
| Arginine (R) | 1 (0.58) | 2 (0.87) |
| Asparagine (N) | 11 (6.43) | 13 (5.65) |
| Aspartic acid (D) | 8 (4.68) | 12 (5.22) |
| Cysteine (C) | 1 (0.58) | 3 (1.30) |
| Glutamic acid (E) | 17 (9.94) | 32 (13.91) |
| Glutamine (Q) | 3 (1.75) | 15 (6.52) |
| Glycine (G) | 15 (8.77) | 13 (5.65) |
| Histidine (H) | 2 (1.17) | 0 (0.00) |
| Isoleucine (I) | 16 (9.36) | 16 (6.96) |
| Leucine (L) | 9 (5.26) | 20 (8.70) |
| Lysine (K) | 25 (14.62) | 43 (18.70) |
| Methionine (M) | 4 (2.34) | 2 (0.87) |
| Phenylalanine (F) | 9 (5.26) | 5 (2.17) |
| Proline (P) | 0 (0.00) | 0 (0.00) |
| Serine (S) | 14 (8.19) | 16 (6.96) |
| Threonine (T) | 10 (5.85) | 14 (6.09) |
| Tryptophan (W) | 1 (0.58) | 1 (0.43) |
| Tyrosine (Y) | 7 (4.09) | 4 (1.74) |
| Valine (V) | 12 (7.02) | 8 (3.48) |
|  | 171 | 230 |

FIG. 3

| | | | | | | | | | | | |
|---|---|---|---|---|---|---|---|---|---|---|---|
| UUU | Phe | 7 | 5 | UCU | Ser | 1 | 4 | UAU | Tyr | 7 | 4 | UGU | Cys | 0 | 2 |
| UUC | Phe | 2 | 0 | UCC | Ser | 0 | 1 | UAC | Tyr | 0 | 0 | UGC | Cys | 1 | 1 |
| UUA | Leu | 5 | 9 | UCA | Ser | 7 | 3 | UAA | *** | 0 | 1 | UGA | *** | 0 | 0 |
| UUG | Leu | 1 | 5 | UCG | Ser | 1 | 0 | UAG | *** | 1 | 0 | UGG | Trp | 1 | 1 |
| CUU | Leu | 2 | 4 | CCU | Pro | 0 | 0 | CAU | His | 2 | 0 | CGU | Arg | 0 | 0 |
| CUC | Leu | 0 | 0 | CCC | Pro | 0 | 0 | CAC | His | 0 | 0 | CGC | Arg | 0 | 0 |
| CUA | Leu | 1 | 1 | CCA | Pro | 0 | 0 | CAA | Gln | 3 | 12 | CGA | Arg | 0 | 0 |
| CUG | Leu | 0 | 1 | CCG | Pro | 0 | 0 | CAG | Gln | 0 | 3 | CGG | Arg | 0 | 0 |
| AUU | Ile | 7 | 8 | ACU | Thr | 5 | 6 | AAU | Asn | 8 | 12 | AGU | Ser | 5 | 5 |
| AUC | Ile | 1 | 0 | ACC | Thr | 0 | 1 | AAC | Asn | 3 | 1 | AGC | Ser | 0 | 3 |
| AUA | Ile | 8 | 8 | ACA | Thr | 4 | 7 | AAA | Lys | 18 | 34 | AGA | Arg | 1 | 2 |
| AUG | Met | 4 | 2 | ACG | Thr | 1 | 0 | AAG | Lys | 7 | 9 | AGG | Arg | 0 | 0 |
| GUU | Val | 7 | 5 | GCU | Ala | 5 | 7 | GAU | Asp | 7 | 11 | GGU | Gly | 6 | 2 |
| GUC | Val | 0 | 1 | GCC | Ala | 0 | 0 | GAC | Asp | 1 | 1 | GGC | Gly | 1 | 0 |
| GUA | Val | 5 | 1 | GCA | Ala | 1 | 3 | GAA | Glu | 12 | 22 | GGA | Gly | 7 | 7 |
| GUG | Val | 0 | 1 | GCG | Ala | 0 | 1 | GAG | Glu | 5 | 10 | GGG | Gly | 1 | 4 |

FIG. 4

```
OspE  M N K K M - -   F I I C A I F A L I V S C K N Y T T S K D L E G S
      · · · ·  · ·    · ·       · ·     · ·    ·   ·  ·  ·    ·
OspF  M N K K M K M F I V Y A V F I L I G A C K I H T - S Y D - E Q S
```

FIG. 7

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 1498 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 129..644

(ix) FEATURE:
        (A) NAME/KEY: CDS
        (B) LOCATION: 672..1364

(xi) SEQUENCE DESCRIPTION: SEQ ID NO: 1:

```
GTTGGTTAAA ATTACATTTG CGTTTTGTTA ATATGTAACA GCTGAATGTA ACAAAATTAT        60

ATATTTAAAT CTTTGAAAAA TTGCAATTAT TATGTATTGT GGTAAGATTA GGACTTATGG       120

AGTAACTT ATG AAT AAG AAA ATG AAA ATG TTT ATT GTT TAT GCT GTT TTT       170
         Met Asn Lys Lys Met Lys Met Phe Ile Val Tyr Ala Val Phe
          1               5                  10

ATA CTT ATA GGT GCT TGC AAG ATT CAT ACT TCA TAT GAT GAG CAA AGT       218
Ile Leu Ile Gly Ala Cys Lys Ile His Thr Ser Tyr Asp Glu Gln Ser
 15                  20                  25                  30

AGT GGT GAG TCA AAA GTT AAA AAA ATA GAA TTC TCT AAA TTT ACT GTA       266
Ser Gly Glu Ser Lys Val Lys Lys Ile Glu Phe Ser Lys Phe Thr Val
```

```
                    35                  40                      45
AAA ATT AAA AAT AAA GAT AAA AGT GGT AAC TGG ACA GAC TTA GGA GAT      314
Lys Ile Lys Asn Lys Asp Lys Ser Gly Asn Trp Thr Asp Leu Gly Asp
                50                  55                      60

TTA GTT GTA AGA AAA GAA GAA AAT GGT ATT GAT ACG GGT TTA AAC GCT      362
Leu Val Val Arg Lys Glu Glu Asn Gly Ile Asp Thr Gly Leu Asn Ala
            65                  70                  75

GGG GGA CAT TCG GCT ACA TTC TTT TCA TTA GAA GAG GAA GTA GTT AAT      410
Gly Gly His Ser Ala Thr Phe Phe Ser Leu Glu Glu Glu Val Val Asn
        80                  85                  90

AAC TTT GTA AAA GTA ATG ACT GAA GGC GGA TCA TTT AAA ACT AGT TTG      458
Asn Phe Val Lys Val Met Thr Glu Gly Gly Ser Phe Lys Thr Ser Leu
95                  100                 105                 110

TAT TAT GGA TAT AAG GAA GAA CAA AGT GTT ATA AAT GGT ATC CAA AAT      506
Tyr Tyr Gly Tyr Lys Glu Glu Gln Ser Val Ile Asn Gly Ile Gln Asn
            115                 120                 125

AAA GAG ATA ATA ACA AAG ATA GAA AAA ATT GAT GGA ACT GAA TAT ATT      554
Lys Glu Ile Ile Thr Lys Ile Glu Lys Ile Asp Gly Thr Glu Tyr Ile
        130                 135                 140

ACA TTT TCA GGA GAT AAA ATT AAG AAT TCA GGA GAT AAA GTT GCT GAA      602
Thr Phe Ser Gly Asp Lys Ile Lys Asn Ser Gly Asp Lys Val Ala Glu
        145                 150                 155

TAT GCA ATA TCA CTA GAA GAG CTT AAG AAG AAT TTA AAA TAGAAGTTGG       651
Tyr Ala Ile Ser Leu Glu Glu Leu Lys Lys Asn Leu Lys
160                 165                 170

AAGTATAGGA GAAAGCTTAT ATG AAT AAA AAA ATG TTT ATT ATT TGT GCT        701
                     Met Asn Lys Lys Met Phe Ile Ile Cys Ala
                      1               5                  10

ATT TTT GCG CTG ATA GTT TCT TGC AAG AAT TAT ACA ACT AGC AAA GAT      749
Ile Phe Ala Leu Ile Val Ser Cys Lys Asn Tyr Thr Thr Ser Lys Asp
            15                  20                  25

TTA GAA GGG TCA GTG CAA GAT TTA GAA AGT TCA GAA CAA AAT GCA AAA      797
Leu Glu Gly Ser Val Gln Asp Leu Glu Ser Ser Glu Gln Asn Ala Lys
        30                  35                  40

AAA ACA GAA CAA GAG ATA AAA AAA CAA GTT GAA GGA TTT TTA GAA ATT      845
Lys Thr Glu Gln Glu Ile Lys Lys Gln Val Glu Gly Phe Leu Glu Ile
        45                  50                  55

CTA GAG ACA AAA GAT TTG AAT ACA TTG AAT ACA AAA GAT ATA AAA GAG      893
Leu Glu Thr Lys Asp Leu Asn Thr Leu Asn Thr Lys Asp Ile Lys Glu
60                  65                  70

ATT GAA AAA CAA ATT CAA GAA TTA AAG GAC ACA ATA AAT AAA TTA GAG      941
Ile Glu Lys Gln Ile Gln Glu Leu Lys Asp Thr Ile Asn Lys Leu Glu
75                  80                  85                  90

GCT AAA AAA ACT TCT CTT AAA ACA TAT TCT GAG TAT GAA GAA CAA ATA      989
Ala Lys Lys Thr Ser Leu Lys Thr Tyr Ser Glu Tyr Glu Glu Gln Ile
                95                  100                 105

AAA AAA ATA AAA GAA AAA TTA AAA GAT AAG AAA GAA CTT GAA GAT AAA      1037
Lys Lys Ile Lys Glu Lys Leu Lys Asp Lys Lys Glu Leu Glu Asp Lys
            110                 115                 120

TTA AAG GAA CTT GAA GAG AGC TTA AAA AAG AAA AAA GAG GAG AGA AAA      1085
Leu Lys Glu Leu Glu Glu Ser Leu Lys Lys Lys Lys Glu Glu Arg Lys
        125                 130                 135

AAA GCT TTA GAA GAT GCT AAG AAG AAA TTT GAA GAG TTT AAA GGA CAA      1133
Lys Ala Leu Glu Asp Ala Lys Lys Lys Phe Glu Glu Phe Lys Gly Gln
        140                 145                 150

GTT GGA TCC GCA ACC GGA CAA ACT CAA GGG CAG AGA GCT GGA AAT CAG      1181
Val Gly Ser Ala Thr Gly Gln Thr Gln Gly Gln Arg Ala Gly Asn Gln
155                 160                 165                 170

GGG CAG GTT GGA CAA CAA GCT TGG AAG TGT GCT AAT AGT TTG GGG TTG      1229
```

-continued

```
Gly Gln Val Gly Gln Gln Ala Trp Lys Cys Ala Asn Ser Leu Gly Leu
            175                 180                 185

GGT GTA AGT TAT TCT AGT AGT ACT GGT ACT GAT AGC AAT GAA TTG GCA      1277
Gly Val Ser Tyr Ser Ser Ser Thr Gly Thr Asp Ser Asn Glu Leu Ala
            190                 195                 200

AAC AAA GTT ATA GAT GAT TCA ATT AAA AAG ATT GAT GAA GAG CTT AAA      1325
Asn Lys Val Ile Asp Asp Ser Ile Lys Lys Ile Asp Glu Glu Leu Lys
            205                 210                 215

AAT ACT ATA GAA AAT AAT GGA GAA GTC AAA AAA GAA TAAAGAAATG           1371
Asn Thr Ile Glu Asn Asn Gly Glu Val Lys Lys Glu
            220                 225                 230

GTTTTTAAAA GTATAAATTA CGAAAAACAA GACTAATAAC CAGTCTTGTT TTTTTATTTA    1431

AGCCATACTT TTATGAAGTG AAAATGCCAA AAACTATTGT TAAAAATGTT GTTTATTTAT    1491

ACATTCT                                                              1498
```

(2) INFORMATION FOR SEQ ID NO: 2:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asn Lys Lys Met Lys Met Phe Ile Val Tyr Ala Val Phe Ile Leu
  1               5                  10                  15

Ile Gly Ala Cys Lys Ile His Thr Ser Tyr Asp Glu Gln Ser Ser Gly
             20                  25                  30

Glu Ser Lys Val Lys Lys Ile Glu Phe Ser Lys Phe Thr Val Lys Ile
         35                  40                  45

Lys Asn Lys Asp Lys Ser Gly Asn Trp Thr Asp Leu Gly Asp Leu Val
     50                  55                  60

Val Arg Lys Glu Glu Asn Gly Ile Asp Thr Gly Leu Asn Ala Gly Gly
 65                  70                  75                  80

His Ser Ala Thr Phe Phe Ser Leu Glu Glu Glu Val Val Asn Phe
                 85                  90                  95

Val Lys Val Met Thr Glu Gly Gly Ser Phe Lys Thr Ser Leu Tyr Tyr
                100                 105                 110

Gly Tyr Lys Glu Glu Gln Ser Val Ile Asn Gly Ile Gln Asn Lys Glu
            115                 120                 125

Ile Ile Thr Lys Ile Glu Lys Ile Asp Gly Thr Glu Tyr Ile Thr Phe
        130                 135                 140

Ser Gly Asp Lys Ile Lys Asn Ser Gly Asp Lys Val Ala Glu Tyr Ala
145                 150                 155                 160

Ile Ser Leu Glu Glu Leu Lys Lys Asn Leu Lys
                165                 170
```

(2) INFORMATION FOR SEQ ID NO: 3:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO: 3:

Met Asn Lys Lys Met Phe Ile Ile Cys Ala Ile Phe Ala Leu Ile Val

```
           1               5                  10                 15
         Ser Cys Lys Asn Tyr Thr Thr Ser Lys Asp Leu Glu Gly Ser Val Gln
                         20                  25                 30

Asp Leu Glu Ser Ser Glu Gln Asn Ala Lys Lys Thr Glu Gln Glu Ile
                     35                  40                  45

Lys Lys Gln Val Glu Gly Phe Leu Glu Ile Leu Glu Thr Lys Asp Leu
                 50                  55                  60

Asn Thr Leu Asn Thr Lys Asp Ile Lys Glu Ile Glu Lys Gln Ile Gln
         65                  70                  75                  80

Glu Leu Lys Asp Thr Ile Asn Lys Leu Glu Ala Lys Lys Thr Ser Leu
                         85                  90                  95

Lys Thr Tyr Ser Glu Tyr Glu Glu Gln Ile Lys Lys Ile Lys Glu Lys
                     100                 105                 110

Leu Lys Asp Lys Lys Glu Leu Glu Asp Lys Leu Lys Glu Leu Glu Glu
                 115                 120                 125

Ser Leu Lys Lys Lys Glu Glu Arg Lys Lys Ala Leu Glu Asp Ala
         130                 135                 140

Lys Lys Lys Phe Glu Glu Phe Lys Gly Gln Val Gly Ser Ala Thr Gly
         145                 150                 155                 160

Gln Thr Gln Gly Gln Arg Ala Gly Asn Gln Gly Val Gly Gln Gln
                         165                 170                 175

Ala Trp Lys Cys Ala Asn Ser Leu Gly Leu Gly Val Ser Tyr Ser Ser
                     180                 185                 190

Ser Thr Gly Thr Asp Ser Asn Glu Leu Ala Asn Lys Val Ile Asp Asp
                 195                 200                 205

Ser Ile Lys Lys Ile Asp Glu Gly Leu Lys Asn Thr Ile Glu Asn Asn
             210                 215                 220

Gly Glu Val Lys Lys Glu
         225                 230

(2) INFORMATION FOR SEQ ID NO: 4:

(i) SEQUENCE CHARACTERISTICS:
          (A) LENGTH: 1361 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: CDS
          (B) LOCATION: 109..1359

(xi) SEQUENCE DESCRIPTION: SEQ ID NO: 4:

AAGCCTAATT CCTTTATAGT AAGAAATAGT GCAATACATA CATTTAGTGT ATGTAAAGTG          60

AGCTATATTT TTATTTAAAC CAATAATTAA ATAGAGGTAA TTTAATTT ATG AAT AAA         117
                                                      Met Asn Lys
                                                        1

ATA GGA ATT GCA TTT ATT ATT AGC TTT CTG TTG TTT GTT AAT TGT AGG          165
Ile Gly Ile Ala Phe Ile Ile Ser Phe Leu Leu Phe Val Asn Cys Arg
    5                  10                  15

GGC AAA TCT TTA GAA GAA GAT TTA AAA AGC ACC ACT TCT AAC AAT AAG          213
Gly Lys Ser Leu Glu Glu Asp Leu Lys Ser Thr Thr Ser Asn Asn Lys
 20                  25                  30                  35
```

```
CAA AAT TTA ATA AGC AAT GAA AAA AAG TCT CTA AAT TCT AAG AAC AAT        261
Gln Asn Leu Ile Ser Asn Glu Lys Lys Ser Leu Asn Ser Lys Asn Asn
             40                  45                  50

AGG CTT AAA GAT TCT CGG TTA AGT AAT TTT GAA AGC AAA AAA AAT GAC        309
Arg Leu Lys Asp Ser Arg Leu Ser Asn Phe Glu Ser Lys Lys Asn Asp
         55                  60                  65

CAG ACA TTA AAA AAA TCC AAA GAC TTT AAA AAG GAT TTA CAA ACT TTA        357
Gln Thr Leu Lys Lys Ser Lys Asp Phe Lys Lys Asp Leu Gln Thr Leu
         70                  75                  80

AGA AAT TCA AAA AAT TTA ATG CCT AAA GAC TTG GAT CAG TCG AGT AAT        405
Arg Asn Ser Lys Asn Leu Met Pro Lys Asp Leu Asp Gln Ser Ser Asn
         85                  90                  95

GAT TTT GAA AAT TTA GAC AAT TCT GAG TCT TTG CAA GAA GCT TCT TCA        453
Asp Phe Glu Asn Leu Asp Asn Ser Glu Ser Leu Gln Glu Ala Ser Ser
100             105                 110                 115

AAG CAC AAT ATT GGC AAG TCA AGA TAC GGT AAA GCT TTG CTG AAA AAT        501
Lys His Asn Ile Gly Lys Ser Arg Tyr Gly Lys Ala Leu Leu Lys Asn
                120                 125                 130

GAT CAC GAT GAG ATT TGG ATT CCC CAT TTA AAC TTG GAA GAA GAC AAA        549
Asp His Asp Glu Ile Trp Ile Pro His Leu Asn Leu Glu Glu Asp Lys
                135                 140                 145

AAT TTT GAG TTT TTC AAG AAA TCT TTG CAA AAC GAT GAG AAT AGA TAT        597
Asn Phe Glu Phe Phe Lys Lys Ser Leu Gln Asn Asp Glu Asn Arg Tyr
        150                 155                 160

GCT CTT GGT GGG TGG CTT TTA AAC AAT GAT GAG GTG TTA GTA AAA TAC        645
Ala Leu Gly Gly Trp Leu Leu Asn Asn Asp Glu Val Leu Val Lys Tyr
        165                 170                 175

AGA TAC AGC GAA AAA GAT GTT AAT CAG TTT TTA ATT GAT ATA GGA AAA        693
Arg Tyr Ser Glu Lys Asp Val Asn Gln Phe Leu Ile Asp Ile Gly Lys
180                 185                 190                 195

AAG CGG TGG GGA GAT TTG TCT TCT AAA ATG AGC ACC TTG GTG CGA TTG        741
Lys Arg Trp Gly Asp Leu Ser Ser Lys Met Ser Thr Leu Val Arg Leu
                200                 205                 210

ATT GGA AAT TAT TCC GAC AAA AGT GAC AGA GAA GAT GAA ATT TCT CTT        789
Ile Gly Asn Tyr Ser Asp Lys Ser Asp Arg Glu Asp Glu Ile Ser Leu
                215                 220                 225

CTG GAT ATG AAT TTG TGT CAA CAA TTT TAT CTA ACC AAG ATT AAT GCT        837
Leu Asp Met Asn Leu Cys Gln Gln Phe Tyr Leu Thr Lys Ile Asn Ala
        230                 235                 240

GGT GGT TCA AGC GCA GAC ATT CTT GTT GCT CTT GAA AAA ACA ATC GAT        885
Gly Gly Ser Ser Ala Asp Ile Leu Val Ala Leu Glu Lys Thr Ile Asp
245                 250                 255

CAA CAA ATT AGC GGT GTT AGC AAA GAA CTT CTT GAA TTA AAA AAT TTT        933
Gln Gln Ile Ser Gly Val Ser Lys Glu Leu Leu Glu Leu Lys Asn Phe
260                 265                 270                 275

TCT CTT ACT ACA AAG TCA GAG CTT GAT TGG TAT TTA AAT TGG AAG CGC        981
Ser Leu Thr Thr Lys Ser Glu Leu Asp Trp Tyr Leu Asn Trp Lys Arg
                280                 285                 290

AAT TTA ACA GAC GAA GAA GAA GAG ACT TTG CAA TGT TGC AGG GTT TTG       1029
Asn Leu Thr Asp Glu Glu Glu Glu Thr Leu Gln Cys Cys Arg Val Leu
                295                 300                 305

TTG GGC GGA GAA TTG GAT TTT GAA AAT CTT GAC GAT TTG TTT AAA AGG       1077
Leu Gly Gly Glu Leu Asp Phe Glu Asn Leu Asp Asp Leu Phe Lys Arg
        310                 315                 320

CTT GGA AAG GAA TAT TCT AGG TTG ATA TTA AGA AAG TTA GAA GAA ATA       1125
Leu Gly Lys Glu Tyr Ser Arg Leu Ile Leu Arg Lys Leu Glu Glu Ile
        325                 330                 335

ACA TTA AAT TAC GAT GTT AAT AGG TTT TTA AAA GAA ATG GAG AAA TCA       1173
Thr Leu Asn Tyr Asp Val Asn Arg Phe Leu Lys Glu Met Glu Lys Ser
340                 345                 350                 355
```

```
CGT AAA TCT TTC AAA CAA GCA TTA GGT TCT ATT AGG AAT AAA AGC AAA    1221
Arg Lys Ser Phe Lys Gln Ala Leu Gly Ser Ile Arg Asn Lys Ser Lys
            360                 365                 370

AGA GTA GTG ATT TTT AAG GTT AGA AAT TCT CTT TTG GAA ATT TTT AAA    1269
Arg Val Val Ile Phe Lys Val Arg Asn Ser Leu Leu Glu Ile Phe Lys
                375                 380                 385

CTT TAT TAC AAC AAT ATT GGC AGG AAT AAA AAA CTT TAT GAT TAT ATA    1317
Leu Tyr Tyr Asn Asn Ile Gly Arg Asn Lys Lys Leu Tyr Asp Tyr Ile
            390                 395                 400

AAT CGC ATG TTA AAC AGC TTG ATA AAA GAG ATT AGC AGG CGT TA         1362
Asn Arg Met Leu Asn Ser Leu Ile Lys Glu Ile Ser Arg Arg
    405                 410                 415
```

(2) INFORMATION FOR SEQ ID NO: 5:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Asn Lys Ile Gly Ile Ala Phe Ile Ile Ser Phe Leu Leu Phe Val
 1               5                  10                  15

Asn Cys Arg Gly Lys Ser Leu Glu Glu Asp Leu Lys Ser Thr Thr Ser
                20                  25                  30

Asn Asn Lys Gln Asn Leu Ile Ser Asn Glu Lys Lys Ser Leu Asn Ser
            35                  40                  45

Lys Asn Asn Arg Leu Lys Asp Ser Arg Leu Ser Asn Phe Glu Ser Lys
        50                  55                  60

Lys Asn Asp Gln Thr Leu Lys Lys Ser Lys Asp Phe Lys Lys Asp Leu
65                  70                  75                  80

Gln Thr Leu Arg Asn Ser Lys Asn Leu Met Pro Lys Asp Leu Asp Gln
                85                  90                  95

Ser Ser Asn Asp Phe Glu Asn Leu Asp Asn Ser Glu Ser Leu Gln Glu
            100                 105                 110

Ala Ser Ser Lys His Asn Ile Gly Lys Ser Arg Tyr Gly Lys Ala Leu
        115                 120                 125

Leu Lys Asn Asp His Asp Glu Ile Trp Ile Pro His Leu Asn Leu Glu
130                 135                 140

Glu Asp Lys Asn Phe Glu Phe Phe Lys Lys Ser Leu Gln Asn Asp Glu
145                 150                 155                 160

Asn Arg Tyr Ala Leu Gly Gly Trp Leu Leu Asn Asn Asp Glu Val Leu
                165                 170                 175

Val Lys Tyr Arg Tyr Ser Glu Lys Asp Val Asn Gln Phe Leu Ile Asp
            180                 185                 190

Ile Gly Lys Lys Arg Trp Gly Asp Leu Ser Ser Lys Met Ser Thr Leu
        195                 200                 205

Val Arg Leu Ile Gly Asn Tyr Ser Asp Lys Ser Asp Arg Glu Asp Glu
        210                 215                 220

Ile Ser Leu Leu Asp Met Asn Leu Cys Gln Gln Phe Tyr Leu Thr Lys
225                 230                 235                 240

Ile Asn Ala Gly Gly Ser Ser Ala Asp Ile Leu Val Ala Leu Glu Lys
                245                 250                 255

Thr Ile Asp Gln Gln Ile Ser Gly Val Ser Lys Glu Leu Leu Glu Leu
            260                 265                 270
```

-continued

```
Lys Asn Phe Ser Leu Thr Thr Lys Ser Glu Leu Asp Trp Tyr Leu Asn
        275                 280                 285

Trp Lys Arg Asn Leu Thr Asp Glu Glu Glu Thr Leu Gln Cys Cys
    290                 295                 300

Arg Val Leu Leu Gly Gly Glu Leu Asp Phe Glu Asn Leu Asp Asp Leu
305                 310                 315                 320

Phe Lys Arg Leu Gly Lys Glu Tyr Ser Arg Leu Ile Leu Arg Lys Leu
                325                 330                 335

Glu Glu Ile Thr Leu Asn Tyr Asp Val Asn Arg Phe Leu Lys Glu Met
            340                 345                 350

Glu Lys Ser Arg Lys Ser Phe Lys Gln Ala Leu Gly Ser Ile Arg Asn
        355                 360                 365

Lys Ser Lys Arg Val Val Ile Phe Lys Val Arg Asn Ser Leu Leu Glu
    370                 375                 380

Ile Phe Lys Leu Tyr Tyr Asn Asn Ile Gly Arg Asn Lys Lys Leu Tyr
385                 390                 395                 400

Asp Tyr Ile Asn Arg Met Leu Asn Ser Leu Ile Lys Glu Ile Ser Arg
                405                 410                 415

Arg (2) INFORMATION FOR SEQ ID NO: 6:

(i) SEQUENCE CHARACTERISTICS:
        (A) LENGTH: 805 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 130..711

(xi) SEQUENCE DESCRIPTION: SEQ ID NO: 6:

TCATATTAAT AAGACCTCCT GTTTCATTTT AACATTTTAA TTGTTTTTAA AGTGTGTACA      60

AAATAAATTA TTTATTGTAA ACTTACTTTT AATTTTAATA TGATTAATAA ATTATAAGGG    120

AGAATTTTT ATG TAT AAA AAT GGT TTT TTT AAA AAC TAT TTG TCA TTG        168
          Met Tyr Lys Asn Gly Phe Phe Lys Asn Tyr Leu Ser Leu
          1               5                   10

CTT TTA ATT TTT TTA GTA ATT GCT TGT ACT TCA AAA GAC AGC TCA AAT      216
Leu Leu Ile Phe Leu Val Ile Ala Cys Thr Ser Lys Asp Ser Ser Asn
    15                  20                  25

GAA TAT GTT GAG GAG CAA GAA GCG GAG AAC TCT TCT AAG CCT GAT GAT      264
Glu Tyr Val Glu Glu Gln Glu Ala Glu Asn Ser Ser Lys Pro Asp Asp
 30                 35                  40                  45

TCT AAA ATA GAT GAA CAT ACT ATT GGG CAT GTT TTT CAC GCT ATG GGA      312
Ser Lys Ile Asp Glu His Thr Ile Gly His Val Phe His Ala Met Gly
                50                  55                  60

GTA GTT CAT TCA AAA AAG GAT CGA AAA AGT TTA GGA GAA AAT ATA AAG      360
Val Val His Ser Lys Lys Asp Arg Lys Ser Leu Gly Glu Asn Ile Lys
            65                  70                  75

GTT TTT TAT TTT TCT GAA GAA GAT GGA CAT TTT CAA ACA ATA CCC TCA      408
Val Phe Tyr Phe Ser Glu Glu Asp Gly His Phe Gln Thr Ile Pro Ser
        80                  85                  90
```

```
AAA GAG AAT GCA AAG TTA ATA GTT TAT TTT TAT GAC AAT GTT TAT GCA      456
Lys Glu Asn Ala Lys Leu Ile Val Tyr Phe Tyr Asp Asn Val Tyr Ala
         95                 100                 105

GGA GAG GCT CCA ATT AGT ATC TCT GGA AAA GAA GCC TTT ATT TTT GTT      504
Gly Glu Ala Pro Ile Ser Ile Ser Gly Lys Glu Ala Phe Ile Phe Val
110                 115                 120                 125

GGG ATT ACC TCT GAC TTT AAA AAG ATT ATA AAC AGC AAT TTA CAT GGC      552
Gly Ile Thr Ser Asp Phe Lys Lys Ile Ile Asn Ser Asn Leu His Gly
                130                 135                 140

GCT AAA AGT GAT CTT ATT GGT ACT TTT AAA GAT CTT AAT ATT AAA AAT      600
Ala Lys Ser Asp Leu Ile Gly Thr Phe Lys Asp Leu Asn Ile Lys Asn
            145                 150                 155

TCA AAA TTG GAA ATT ACA GTT GAT GAG AAT AAT TCA GAT GCC AAG ACT      648
Ser Lys Leu Glu Ile Thr Val Asp Glu Asn Asn Ser Asp Ala Lys Thr
                160                 165                 170

TTC CTT GAA TCT GTT AAT TAC ATT ATC GAC GGC GTT GAA AAA ATT TCA      696
Phe Leu Glu Ser Val Asn Tyr Ile Ile Asp Gly Val Glu Lys Ile Ser
        175                 180                 185

CCT ATG TTA ACG AAT TAATTTATAT TTTTGATTTT ATAGGCTTTA ATCTAAATTA      751
Pro Met Leu Thr Asn
190

AAGCCTATTT TAAAAAATCA AGCTCTCAAG TCCTTTTATT AAAATTTCTG CTGT          805

(2) INFORMATION FOR SEQ ID NO: 7:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO: 7:

Met Tyr Lys Asn Gly Phe Phe Lys Asn Tyr Leu Ser Leu Leu Ile
1               5                   10                  15

Phe Leu Val Ile Ala Cys Thr Ser Lys Asp Ser Ser Asn Glu Tyr Val
                20                  25                  30

Glu Glu Gln Glu Ala Glu Asn Ser Ser Lys Pro Asp Asp Ser Lys Ile
            35                  40                  45

Asp Glu His Thr Ile Gly His Val Phe His Ala Met Gly Val Val His
        50                  55                  60

Ser Lys Lys Asp Arg Lys Ser Leu Gly Glu Asn Ile Lys Val Phe Tyr
65                  70                  75                  80

Phe Ser Glu Glu Asp Gly His Phe Gln Thr Ile Pro Ser Lys Glu Asn
                85                  90                  95

Ala Lys Leu Ile Val Tyr Phe Tyr Asp Asn Val Tyr Ala Gly Glu Ala
            100                 105                 110

Pro Ile Ser Ile Ser Gly Lys Glu Ala Phe Ile Phe Val Gly Ile Thr
        115                 120                 125

Ser Asp Phe Lys Lys Ile Ile Asn Ser Asn Leu His Gly Ala Lys Ser
    130                 135                 140

Asp Leu Ile Gly Thr Phe Lys Asp Leu Asn Ile Lys Asn Ser Lys Leu
145                 150                 155                 160

Glu Ile Thr Val Asp Glu Asn Asn Ser Asp Ala Lys Thr Phe Leu Glu
                165                 170                 175

Ser Val Asn Tyr Ile Ile Asp Gly Val Glu Lys Ile Ser Pro Met Leu
            180                 185                 190

Thr Asn
```

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

TCGTGGGATC CAAGATTCAT ACTTCATATG AT                              32

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

GACTTCTCGA GCTATTTTAA ATTCTTCTTA AG                              32

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

TCGTGGAATT CAAGAATTAT ACAACTAGCA AA                              32

(2) INFORMATION FOR SEQ ID NO: 11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

TCGAGTTATT CTTTTTTGAC TTCTCC                                        26

B. BURGDORFERI POLYPEPTIDES

This application claims priority under 35 U.S.C. § 120 as a divisional of U.S. application Ser. No. 08/909,119, filed Aug. 11, 1997, now U.S. Pat. No. 5,807,685, which is a divisional of U.S. application Ser. No. 08/118,469, filed Sep. 8, 1993, now U.S. Pat. No. 5,656,451, which is a continuation in part of U.S. application Ser. No. 08/099,757, filed Jul. 30, 1993, now abandoned.

TECHNICAL FIELD OF THE INVENTION

This invention relates to compositions and methods useful for the prevention, diagnosis and treatment of Lyme disease. More particularly, this invention relates to novel *B. burgdorferi* polypeptides which are able to elicit in a treated animal, the formation of an immune response which is effective to prevent or lessen the severity, for some period of time, of *B. burgdorferi* infection. This invention also relates to multicomponent vaccines comprising one or more of the novel *B. burgdorferi* polypeptides. Also within the scope of this invention are antibodies directed against the novel *B. burgdorferi* polypeptides and diagnostic kits comprising the antibodies or the polypeptides.

BACKGROUND OF THE INVENTION

Lyme borreliosis is the most common vector-borne infection in the United States [S. W. Barthold, et al., "An Animal Model For Lyme Arthritis", *Ann. N.Y. Acad. Sci.*, 539, pp. 264–73 (1988)]. It has been reported in every continent except Antarctica. The clinical hallmark of Lyme Disease is an early expanding skin lesion known as erythema migrans, which may be followed weeks to months later by neurologic, cardiac, and joint abnormalities.

The causative agent of Lyme disease is a spirochete known as Borrelia burgdorferi, transmitted primarily by Ixodes ticks of the Ixodes ricinus complex. *B. burgdorferi* has also been shown to be carried in other species of ticks and in mosquitoes and deer flies, but it appears that only ticks of the I. ricinus complex are able to transmit the disease to humans.

Lyme disease generally occurs in three stages. Stage one involves localized skin lesions (erythema migrans) from which the spirochete is cultured more readily than at any other time during infection [B. W. Berger et al., "Isolation And Characterization Of The Lyme Disease Spirochete From The Skin Of Patients With Erythema Chronicum Migrans", *J. Am. Acad. Dermatol.*, 3, pp. 444–49 (1985)]. Flu-like or meningitis-like symptoms are common at this time. Stage two occurs within days or weeks, and involves spread of the spirochete through the patient's blood or lymph to many different sites in the body including the brain and joints. Varied symptoms of this disseminated infection occur in the skin, nervous system, and musculoskeletal system, although they are typically intermittent. Stage three, or late infection, is defined as persistent infection, and can be severely disabling. Chronic arthritis, and syndromes of the central and peripheral nervous system appear during this stage, as a result of the ongoing infection and perhaps a resulting auto-immune disease [R. Martin et al., "*Borrelia burgdorferi*-Specific And Autoreactive T-Cell Lines From Cerebrospinal Fluid In Lyme Radiculomyelitis", *Ann Neurol.*, 24, pp. 509–16 (1988)].

*B. burgdorferi* is much easier to culture from the tick than from humans, therefore at present, Lyme disease is diagnosed primarily by serology. The enzyme-linked immunosorbent assay (ELISA) is one method of detection, using sonicated whole spirochetes as the antigen [J. E. Craft et al., "The Antibody Response In Lyme Disease: Evaluation Of Diagnostic Tests", *J. Infect. Dis.*, 149, pp. 789–95 (1984)]. However, false negative and, more commonly, false positive results are associated with currently available tests.

At present, all stages of Lyme disease are treated with antibiotics. Treatment of early disease is usually effective, however the cardiac, arthritic, and nervous system disorders associated with the later stages often do not respond to therapy [A. C. Steere, "Lyme Disease", *New Eng. J. Med.*, 321, pp. 586–96 (1939)].

Like *Treponema pallidum*, which causes syphilis, and leptospirae, which cause an infectious jaundice, Borrelia belong to the eubacterial phylum of spirochetes [A. G. Barbour and S. F. Hayes, "Biology Of Borrelia Species", *Microbiol. Rev.*, 50, pp. 381–400 (1986)]. *Borrelia burgdorferi* have a protoplasmic cylinder that is surrounded by a cell membrane, then by flagella, and then by an outer membrane.

The *B. burgdorferi* outer surface proteins identified to date are believed to be lipoproteins, as demonstrated by labelling with [$^3$H]palmitate [M. E. Brandt et al., "Immunogenic Integral membrane Proteins of *Borrelia burgdorferi* Are Lipoproteins", *Infect. Immun.*, 58, pp. 983–91 (1990)]. The two major outer surface proteins are the 31 kd outer-surface protein A (OspA) and the 34 kd outer surface protein B (OspB). Both proteins have been shown to vary from different isolates or from different passages of the same isolate as determined by their molecular weights and reactivity with monoclonal antibodies OspC is a 22 kDa membrane lipoprotein previously identified as pC. [R. Fuchs et al., "Molecular Analysis and Expression of a *Borrelia burgdorferi* Gene Encoding a 22 kDa Protein (pC) in *Escherichia coli*", *Mol. Microbiol.*, 6, pp. 503–09 (1992)]. OspD is said to be preferentially expressed by low-passage, virulent strains of *B. burgdorferi* B31 [S. J. Norris et al., "Low-Passage-Associated Proteins of *Borrelia burgdorferi* B31: Characterization and Molecular Cloning of OspD, A Surfaced-Exposed, Plasmid-Encoded Lipoprotein", *Infect. Immun.*, 60, pp. 4662–4672 (1992)].

Non-Osp *B. burgdorferi* proteins identified to date include the 41 kD flagellin protein, which is known to contain regions of homology with other bacterial flagellins [G. S. Gassman et al., "Analysis of the *Borrelia burgdorferi* GeHo fla Gene and Antigenic Characterization of Its Gene Product.", *J. Bacteriol.*, 173, pp. 1452–59 (1991)] and a 93kDa protein said to be localized to the periplasmic space [D. J. Volkman et al., "Characterization of an Immunoreactive 93 kDa Core Protein of *Borrelia burgdorferi* With a Human IgG Monoclonal Antibody", *J. Immun.*, 146, pp. 3177–82 (1991)].

Recently, immunization of mice with recombinant OspA has been shown to be effective to confer long-lasting protection against subsequent infection with *B. burgdorferi* [E. Fikrig et al., "Long-Term Protection of Mice from Lyme Disease by Vaccination:with OspA", *Infec. Immun.*, 60, pp. 773–77 (1992)]. However, protection by the OspA immunogens used to date appears to be somewhat strain specific, probably due to the heterogeneity of the OspA gene among different *B. burgdorferi* isolates. For example, immunization with OspA from *B. burgdorferi* strain N40 confers protection against subsequent infection with strains N40, B31 and CD16, but not against strain 25015 [E. Fikrig et al., "*Borrelia burgdorferi* Strain 25015: Characterization of Outer Surface Protein A and Vaccination Against Infection", *J. Immun.*, 148, pp. 2256–60 (1992)].

Immunization with OspB has also been shown to confer protection against Lyme disease but not to the same extent as that conferred by OspA [E. Fikrig et al., "Roles of OspA, OspB, and Flagellin in Protective Immunity to Lyme Borreliosis in Laboratory Mice", *Infec. Immun.*, 60, pp. 657–61 (1992)]. Moreover, some *B. burgdorferi* are apparently able to escape destruction in OspB-immunized mice via a mutation in the OspB gene which results in expression of a truncated OspB protein [E. Fikrig et al., "Evasion of Protective Immunity by *Borrelia burgdorferi* by Truncation of Outer Surface Protein B", *Proc. Natl. Acad. Sci.*, 90, pp. 4092–96 (1993)]. OspC has also been shown to have protective effects in a gerbil model of *B. burgdorferi* infection. However, the protection afforded by immunization with this protein appears to be only partial [V. Preac-Mursic et al., "Active Immunization with pC Protein of *Borrelia burgdorferi* Protects Gerbils against *B. burgdorferi* Infection", *Infection*, 20, pp. 342–48 (1992)].

As prevention of tick infestation is imperfect, and Lyme disease may be missed or misdiagnosed when it does appear, there exists a continuing urgent need for the determination of additional antigens of *B. burgdorferi* and related proteins which are able to elicit a protective immune response and which may be useful in a broad-spectrum vaccine. In addition, identification of additional *B. burgdorferi* antigens may enable the development of more reliable diagnostic reagents which are useful in various stages of Lyme borreliosis.

DISCLOSURE OF THE INVENTION

The present invention provides novel *B. burgdorferi* polypeptides which are substantially free of a *B. burgdorferi* spirochete or fragments thereof and which are thus useful in compositions and methods for the diagnosis, treatment and prevention of *B. burgdorferi* infection and Lyme disease. In one preferred embodiment, this invention provides OspE polypeptides and pharmaceutically effective compositions and methods comprising those polypeptides.

In another preferred embodiment, this invention provides OspF polypeptides and pharmaceutically effective compositions and methods comprising those polypeptides.

In another preferred embodiment, this invention provides S1 polypeptides and pharmaceutically effective compositions and methods comprising those polypeptides.

In another preferred embodiment, this invention provides T5 polypeptides and pharmaceutically effective compositions and methods comprising those polypeptides.

The preferred compositions and methods of each of the aforementioned embodiments are characterized by novel *B. burgdorferi* polypeptides which elicit in treated animals, the formation of an immune response which is effective to prevent or lessen the severity, for some period of time, of *B. burgdorferi* infection.

In another preferred embodiment, this invention provides a multicomponent vaccine comprising one or more novel *B. burgdorferi* polypeptides of this invention in addition to one or more other immunogenic *B. burgdorferi* polypeptides. Such a vaccine is effective to confer broad protection against *B. burgdorferi* infection.

In yet another embodiment, this invention provides antibodies directed against the novel *B. burgdorferi* polypeptides of this invention, and pharmaceutically effective compositions and methods comprising those antibodies.

In another embodiment, this invention provides diagnostic means and methods characterized by one or more of the novel *B. burgdorferi* polypeptides, or antibodies directed against those polypeptides. These means and methods are useful for the detection of Lyme disease and *B. burgdorferi* infection. They are also useful in following the course of treatment against such infection. In patients previously inoculated with the vaccines of this invention, the detection means and methods disclosed herein are also useful for determining if booster inoculations are appropriate.

In yet another embodiment, this invention provides methods for identification and isolation of additional *B. burgdorferi* polypeptides, as well as compositions and methods comprising such polypeptides.

Finally, this invention provides DNA sequences that code for the novel *B. burgdorferi* polypeptides of this invention, recombinant DNA molecules that are characterized by those DNA sequences, unicellular hosts transformed with those DNA sequences and molecules, and methods of using those sequences, molecules and hosts to produce the novel *B. burgdorferi* polypeptides and multicomponent vaccines of this invention. DNA sequences of this invention are also advantageously used in methods and means for the diagnosis of Lyme disease and *B. burgdorferi* infection.

BRIEF DESCRIPTION OF THE DRAWINGS

FIG. 2 depicts a comparison of the control regions of transcription and translation among the DNA sequences encoding the novel *B. burgdorferi* polypeptides of this invention and the DNA sequences of other known *B. burgdorferi* outer surface proteins. The consensus "−35" and "−10" sigma 70-like promoter sequences and consensus ribosomal binding sequence are from *E. coli*. The OspA and OspB sequences are from the OspA-B operon of *B. burgdorferi* strain B31. OspC sequences are from strain PKo. OspD sequences are from strain B31.

FIG. 3 depicts the amino acid composition of the deduced OspE and OspF proteins. For each amino acid, the number outside the parentheses indicates the total number of that particular amino acid; the number inside the parentheses refers to the percent of the total amino acid sequence composed of that amino acid.

FIG. 4 depicts the codon usage of the OspE and OspF genes in *B. burgdorferi* N40. The preferred codons in *B. burgdorferi* OspA-B31, OspB-B31, OspC-PKo and OspD-B31 are underlined and bolded.

FIG. 7 depicts a comparison of the N-terminal 30 amino acids of OspE and OspF. Identical amino acids are indicated with an asterisk. The cleavage signal recognized by *B. burgdorferi* signal peptidase is underlined and shown in bold letters.

DETAILED DESCRIPTION OF THE INVENTION

Figure 1:
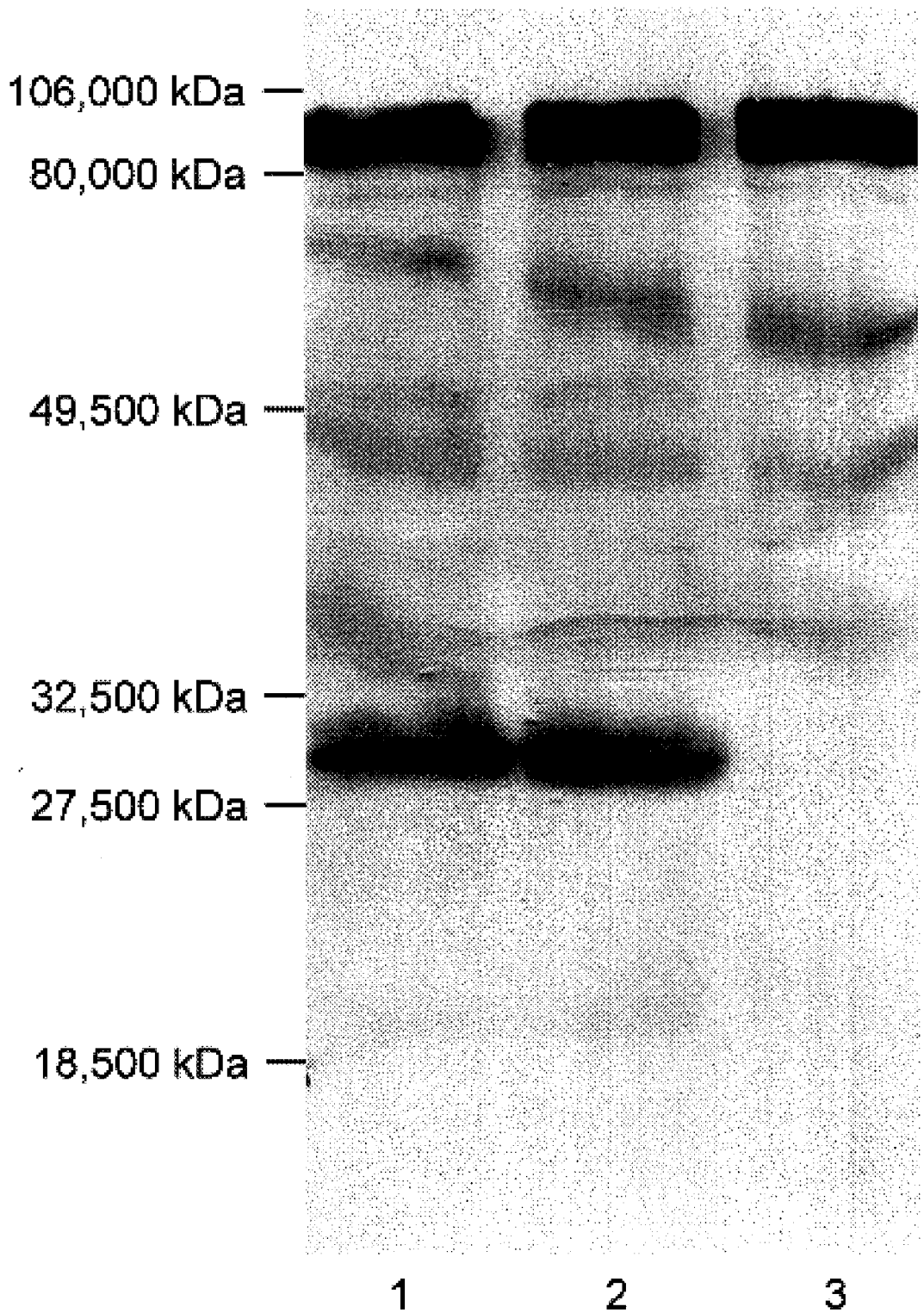
FIG. 1 depicts an immunoblot of protein extracts from cells transformed with clone #11. The blot is probed with combined mouse anti-OspE and anti-OspF antiserum. Lane 1—uninduced clone #11; Lane 2—clone #11, induced; Lane 3—XL-1 Blue cells, uninduced.

This invention relates to novel *B. burgdorferi* polypeptides and the DNA sequences which encode them, antibodies directed against those polypeptides, compositions comprising the polypeptides or antibodies, and methods for the detection, treatment and prevention of Lyme disease.

More specifically, in one embodiment, this invention relates to compositions and methods comprising OspE polypeptides. The preferred compositions and methods of this embodiment comprise immunogenic OspE polypeptides that elicit in treated animals an immune response which is effective to decrease the level of *B. burgdorferi* spirochetes in ticks feeding on such animals.

In another embodiment, this invention relates to compositions and methods comprising OspF polypeptides. The preferred compositions and methods of this embodiment comprise immunogenic OspF polypeptides that elicit in treated animals an immune response which is effective to prevent or lessen the severity, for some period of time, of *B. burgdorferi* infection. Immunogenic OspF polypeptides are not only capable of eliciting, in treated animals, an immune response which is effective to decrease the level of *B. burgdorferi* spirochetes in ticks feeding on such animals, but are also effective to protect the animal against *B. burgdorferi* infection and against Lyme disease-related disorders which would normally result from such infection.

In another embodiment, this invention relates to S1 polypeptides and pharmaceutically effective compositions and methods comprising those polypeptides.

In another embodiment, this invention relates to T5 polypeptides and pharmaceutically effective compositions and methods comprising those polypeptides.

The preferred compositions and methods of each of the aforementioned embodiments are characterized by novel *B. burgdorferi* polypeptides which are also immunogenic *B. burgdorferi* polypeptides i.e., which elicit in treated animals, the formation of an immune response which is effective to prevent or lessen the severity, for some period of time, of *B. burgdorferi* infection.

In another embodiment, this invention relates to a multicomponent vaccine against Lyme disease comprising one or more of the novel *B. burgdorferi* polypeptides of this invention in addition to other immunogenic *B. burgdorferi* polypeptides. Such vaccine is useful to protect against infection by a broad spectrum of *B. burgdorferi* organisms.

All of the novel *B. burgdorferi* polypeptides provided by this invention, and the DNA sequences encoding them, are substantially free of a *B. burgdorferi* spirochete or fragments thereof, and thus may be used in a variety of applications without the risk of unintentional infection or contamination with undesired *B. burgdorferi* components. Accordingly, the novel *B. burgdorferi* polypeptides of this invention are particularly advantageous in compositions and methods for the diagnosis and prevention of *B. burgdorferi* infection.

In another embodiment, this invention relates to compositions and methods comprising antibodies directed against the novel *B. burgdorferi* polypeptides of this invention. Such antibodies may be used in a variety of applications, including to detect the presence of *B. burgdorferi*, to screen for expression of novel *B. burgdorferi* polypeptides, to purify novel *B. burgdorferi* polypeptides, to block or bind to the novel *B. burgdorferi* polypeptides, to direct molecules to the surface of *B. burgdorferi* and to prevent or lessen the severity, for some period of time, of *B. burgdorferi* infection.

In still another embodiment, this invention relates to diagnostic means and methods characterized by the novel *B. burgdorferi* polypeptides disclosed herein or antibodies directed against those polypeptides.

In order to further define this invention, the following terms and definitions are herein provided.

As used herein, an "immunogenic *B. burgdorferi* polypeptide" is any *B. burgdorferi* molecule that, when administered to an animal, is capable of eliciting an immune response that is effective to prevent or lessen the severity, for some period of time, of *B. burgdorferi* infection. Preventing or lessening the severity of infection may be evidenced by a change in the physiological manifestations of erythema migrans, arthritis, carditis, neurological disorders, and other Lyme disease related disorders. It may be evidenced by a decrease in or absence of-spirochetes in the treated animal. And, it may be evidenced by a decrease in the level of spirochetes in infected ticks which have fed on treated animals.

Immunogenic *B. burgdorferi* polypeptides are intended to include not only the novel *B. burgdorferi* polypeptides of this invention but also the OspA and OspB polypeptides disclosed in PCT patent application WO 92/00055; the OspC protein as described in R. Fuchs et al., supra; other *B. burgdorferi* proteins; and fragments, serotypic variants and derivatives of any of the above. In particular, immunogenic *B. burgdorferi* polypeptides are intended to include additional *B. burgdorferi* polypeptides which may also be identified according to the methods disclosed herein.

As used herein, a polypeptide which is "substantially free of a *B. burgdorferi* spirochete or fragments thereof" is a polypeptide that, when introduced into modified Barbour-Stoener-Kelly (BSK-II) medium and cultured at 37° C. for 7 days, fails to produce any *B. burgdorferi* spirochetes detectable by dark field microscopy or a polypeptide that is detectable as a single band on an immunoblot probed with polyclonal anti-*B. burgdorferi* anti-serum.

As used herein, an "OspE polypeptide" denotes a polypeptide which is substantially free of *B. burgdorferi* spirochete or fragments thereof and which is selected from the group consisting of:

(a) an OspE protein consisting of amino acids 1–171 of SEQ ID NO: 2 and serotypic variants thereof;

(b) fragments comprising at least 8 amino acids taken as a block from the OspE polypeptide of (a);

(c) derivatives of an OspE polypeptide of (a) or (b), said derivatives being at least 80% identical in amino acid sequence to the corresponding polypeptide of (a) or (b);

(d) polypeptides that are immunologically reactive with antibodies generated by infection of a mammalian host with *B. burgdorferi*, which antibodies are immunologically reactive with an OspE polypeptide of (a) or (b) or (c); (e) polypeptides that are capable of eliciting antibodies that are immunologically reactive with *B. burgdorferi* and the OspE polypeptide of (a) or (b) or (c); and (f) polypeptides that are immunologically reactive with antibodies elicited by immunization with the OspE polypeptide of (a) or (b) or (c).

As used herein, a "serotypic variant" of an OspE polypeptide is any naturally occurring polypeptide which may be encoded in whole or in part, by a DNA sequence which hybridizes, at 20–27° C. below Tm, to the DNA sequence encoding the OspE protein of SEQ ID NO: 2. One of skill in the art will understand that serotypic variants of an OspE polypeptide include polypeptides encoded by DNA sequences of which any portion may be amplified by using the polymerase chain reaction and oligonucleotide primers derived from any portion of the DNA sequence encoding the OspE protein of SEQ ID NO: 2.

As used herein, an "OspF polypeptide" denotes a polypeptide which is substantially free of a *B. burgdorferi* spirochete or fragments thereof and which is selected from the group consisting of:

(a) an OspF protein consisting of amino acids 1–230 of SEQ ID NO: 3 and serotypic variants thereof;

(b) fragments comprising at least 8 amino acids taken as a block from the OspF polypeptide of (a);

(c) derivatives of the OspF polypeptide of (a) or (b), said derivatives being at least 80% identical in amino acid sequence to the corresponding polypeptide of (a) or (b);

(d) polypeptides that are immunologically reactive with antibodies generated by infection of a mammalian host with *B. burgdorferi*, which antibodies are immunologically reactive with an OspF polypeptide of (a) or (b) or (c);

(e) polypeptides that are capable of eliciting antibodies that are immunologically reactive with *B. burgdorferi* and the OspF polypeptide of (a) or (b) or (c); and (f) polypeptides that are immunologically reactive with antibodies elicited by immunization with the OspF polypeptide of (a) or (b) or (c).

As used herein, a "serotypic variant" of an OspF polypeptide is any naturally occurring polypeptide which may be encoded, in whole or in part, by a DNA sequence which hybridizes, at 20–27° C. below Tm, to the DNA sequence encoding the OspF protein of SEQ ID NO: 3. As with serotypic variants of OspE polypeptides, one of skill in the art will readily appreciate that serotypic variants of OspF polypeptides include those polypeptides encoded by *B. burgdorferi* DNA sequences of which any portion may be amplified by using the polymerase chain reaction and oligonucleotide primers derived from any portion of the DNA sequence encoding the OspF protein of SEQ ID NO: 3.

As used herein, an "S1 polypeptide" denotes a polypeptide which is substantially free of a *B. burgdorferi* spirochete or fragments thereof and which is selected from the group consisting of:

(a) an S1 protein having the amino acid sequence of SEQ ID NO: 5 and serotypic variants thereof;

(b) fragments comprising at least 8 amino acids taken as a block from the S1 polypeptide of (a);

(c) derivatives of the S1 polypeptide of (a) or (b), said derivatives being at least 80% identical in amino acid sequence to the corresponding polypeptide of (a) or (b);

(d) polypeptides that are immunologically reactive with antibodies generated by infection of a mammalian host with *B. burgdorferi*, which antibodies are immunologically reactive with an S1 polypeptide of (a) or (b) or (c);

(e) polypeptides that are capable of eliciting antibodies that are immunologically reactive with *B. burgdorferi* and the S1 polypeptide of (a) or (b) or (c); and (f) polypeptides that are immunologically reactive with antibodies elicited by immunization with the S1 polypeptide of (a) or (b) or (c).

As used herein, a "serotypic variant" of an S1 polypeptide is any naturally occurring polypeptide which may be encoded, in whole or in part, by a DNA sequence which hybridizes, at 20–27° C. below Tm, to the DNA sequence encoding the S1 protein SEQ ID NO: 5. Again, serotypic variants of S1 polypeptides include those polypeptides encoded by *B. burgdorferi* DNA sequences of which any portion may be amplified by using the polymerase chain reaction and oligonucleotide primers derived from any portion of the DNA sequence encoding the S1 protein of SEQ ID NO: 5.

As used herein, a "T5 polypeptide" denotes a polypeptide which is substantially free of a *B. burgdorferi* spirochete or fragments thereof and which is selected from the group consisting of:

(a) a T5 polypeptide having the amino acid sequence of SEQ ID NO: 7 and serotypic variants thereof;

(b) fragments comprising at least 8 amino acids taken as a block from the T5 polypeptide of (a);

(c) derivatives of the T5 polypeptide of (a) or (b) said derivatives being at least 80% identical in amino acid sequence to the corresponding polypeptide of (a) or (b);

(d) polypeptides that are immunologically-reactive with antibodies generated by infection of a mammalian host with *B. burgdorferi*, which antibodies are immunologically reactive with a T5 polypeptide of (a) or (b) or (c);

(e) polypeptides that are capable of eliciting antibodies that are immunologically reactive with *B. burgdorferi* and the T5 polypeptide of (a) or (b) or (c); and (f) polypeptides that are immunologically reactive with antibodies elicited by immunization with the T5 polypeptide of (a) or (b) or (c).

As used herein, a "serotypic variant" of a T5 polypeptide is any naturally occurring polypeptide which may be encoded, in whole or in part, by a DNA sequence which hybridizes, at 20–27° C. below Tm, to the DNA sequence encoding the T5 protein SEQ ID NO: 7. Again, serotypic variants of T5 polypeptides include those polypeptides encoded by *B. burgdorferi* DNA sequences of which any portion may be amplified by using the polymerase chain reaction and oligonucleotide primers derived from any portion of the DNA sequence encoding the T5 protein of SEQ ID NO: 7.

As used herein, a "novel *B. burgdorferi* polypeptide" is an OspE polypeptide, an OspF polypeptide, an S1 polypeptide, a T5 polypeptide, or one or more *B. burgdorferi* polypeptides encoded in whole or in part by a DNA sequence present in clone 4, 5 or 7 as described in Example XV, infra.

As used herein, a "derivative" a novel *B. burgdorferi* polypeptide is a polypeptide in which one or more physical, chemical, or biological properties has been altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

As used herein, a "protective antibody" is an antibody that confers protection, for some period of time, against any one of the physiological disorders associated with *B. burgdorferi* infection.

As used herein, a "protective epitope" is (1) an epitope which is recognized by a protective antibody, and/or (2) an epitope which, when used to immunize an animal, elicits an immune response sufficient to prevent or lessen the severity for some period of time, of *B. burgdorferi* infection. Again, preventing or lessening the severity of infection may be evidenced by a change in the physiological manifestations of erythema migrans, arthritis, carditis, neurological disorders, and other Lyme disease related disorders. It may be evidenced by a decrease in the level of spirochetes in the treated animal. And, it may also be evidenced by a decrease in the level of spirochetes in infected ticks feeding on treated animals. A protective epitope may comprise a T cell epitope, a B cell epitope, or combinations thereof.

As used herein, a "T cell epitope" is an epitope which, when presented to T cells by antigen presenting cells, results in a T cell response such as clonal expansion or expression of lymphokines or other immunostimulatory molecules. A T cell epitope may also be an epitope recognized by cytotoxic T cells that may affect intracellular *B. burgdorferi* infection. A strong T cell epitope is a T cell epitope which elicits a strong T cell response.

As used herein, a "B cell epitope" is the simplest spatial conformation of an antigen which reacts with a specific antibody.

As used herein, a "therapeutically effective amount" of a polypeptide or of an antibody is the amount that, when administered to an animal, elicits an immune response that is effective to prevent or lessen the severity, for some period of time, of *B. burgdorferi* infection.

As used herein, an "anti-OspE polypeptide antibody" is an immunoglobulin molecule or portion thereof, that is immunologically reactive with an OspE polypeptide of the present invention, and that was either elicited by immunization with an OspE polypeptide of this invention or was isolated or identified by its reactivity with an OspE polypeptide of this invention.

As used herein, an "anti-OspF polypeptide antibody" is an immunoglobulin molecule, or portion thereof, that is immunologically reactive with an OspF polypeptide of the present invention and that was either elicited by immunization with an OspF polypeptide of this invention or was isolated or identified by its reactivity with an OspF polypeptide of this invention.

As used herein an "anti-S1 polypeptide antibody" is an immunoglobulin molecule, or portion thereof, that is immunologically reactive with an S1 polypeptide of the present invention and that was either elicited by immunization with an S1 polypeptide of this invention or was isolated or identified by its reactivity with an S1 polypeptide of this invention.

As used herein an "anti-T5 polypeptide antibody" is an immunoglobulin molecule, or portion thereof, that is immunologically reactive with a T5 polypeptide of the present invention and that was either elicited by immunization with a T5 polypeptide of this invention or was isolated or identified by its reactivity with a T5 polypeptide of this invention.

As used herein, an "antibody directed against a novel *B. burgdorferi* polypeptide" (also referred to as "an antibody of this invention") is an anti-OspE polypeptide antibody, an anti-OspF polypeptide antibody, an anti-S1 polypeptide antibody or an anti-T5 polypeptide antibody. It should be understood that an antibody directed against a novel *B. burgdorferi* polypeptide may also be a protective antibody.

It should also be understood that the antibodies of this invention are not intended to include those antibodies which are normally elicited in an animal upon infection with naturally occurring *B. burgdorferi* and which have not been removed from or altered within the animal in which they were elicited.

An antibody directed against a novel *B. burgdorferi* polypeptide may be an intact immunoglobulin molecule or a portion of an immunoglobulin molecule that contains an intact antigen binding site, including those portions known in the art as F(v), Fab, Fab' and F(ab')2. It may also be a genetically engineered or synthetically produced molecule.

The novel *B. burgdorferi* polypeptides disclosed herein are immunologically reactive with antisera generated by infection of a mammalian host with *B. burgdorferi*. Accordingly, they are useful in methods and compositions to diagnose and protect against Lyme disease, and in therapeutic compositions to stimulate immunological clearance of *B. burgdorferi* during ongoing infection. In addition, because at least some, if not all of the novel *B. burgdorferi* polypeptides disclosed herein are immunogenic surface proteins of *B. burgdorferi*, they are particularly useful in a multicomponent vaccine against Lyme disease, because such a vaccine may be formulated to more closely resemble the immunogens presented by replication-competent *B. burgdorferi*, and because such a vaccine is more likely to confer broad-spectrum protection than a vaccine comprising only a single *B. burgdorferi* polypeptide. Multicomponent vaccines according to this invention may also contain polypeptides which characterize any currently existing or to be discovered vaccine useful for immunization of diseases other than Lyme disease such as, for example, diphtheria, polio, hepatitis, and measles. Such multicomponent vaccines are characterized by a single composition form.

The preferred compositions and methods of this invention comprise novel *B. burgdorferi* polypeptides having enhanced immunogenicity. Such polypeptides may result when the native forms of the polypeptides or fragments thereof are modified or subjected to treatments to enhance their immunogenic character in the intended recipient.

Numerous techniques are available and well known to those of skill in the art which may be used, without undue experimentation, to substantially increase the immunogenicity of the novel *B. burgdorferi* polypeptides herein disclosed. For example, the polypeptides may be modified by coupling to dinitrophenol groups or arsanilic acid, or by denaturation with heat and/or SDS.

Particularly if the polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see *Antibodies, A Laboratory Manual*, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads.; activated carbon; or bentonite.

Modification of the amino acid sequence of the novel *B. burgdorferi* polypeptides disclosed herein in order to alter the lipidation state is also a method which may be used to increase their immunogenicity and biochemical properties. For example, the polypeptides or fragments thereof may be expressed with or without the signal sequences that direct addition of lipid moieties.

As will be apparent from the disclosure to follow, the polypeptides may also be prepared with the objective of increasing stability or rendering the molecules more amenable to purification and preparation. One such technique is to express the polypeptides as fusion proteins comprising other *B. burgdorferi* or non-*B. burgdorferi* sequences.

In accordance with this invention, derivatives of the novel *B. burgdorferi* polypeptides may be prepared by a variety of methods, including by in vitro manipulation of the DNA encoding the native polypeptides and subsequent expression of the modified DNA, by chemical synthesis of derivatized DNA sequences, or by chemical or biological manipulation of-expressed amino acid sequences.

For example, derivatives may be produced by substitution of one or more amino acids with a different natural amino acid, an amino acid derivative or non-native amino acid, conservative substitution being preferred, e.g., 3-methylhistidine may be substituted for histidine, 4-hydroxyproline may be substituted for proline, 5-hydroxylysine may be substituted for lysine, and the like.

Causing amino acid substitutions which are less conservative may also result in desired derivatives, e.g., by causing changes in charge, conformation and other biological properties. Such substitutions would include for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

In a preferred embodiment of this invention, the novel *B. burgdorferi* polypeptides disclosed herein are prepared as part of a larger fusion protein. For example, a novel *B. burgdorferi* polypeptide of this invention may be fused at its N-terminus or C-terminus to a different immunogenic *B. burgdorferi* polypeptide, to a non-*B. burgdorferi* polypeptide or to combinations thereof, to produce fusion proteins comprising the novel *B. burgdorferi* polypeptide.

In a preferred embodiment of this invention, fusion proteins comprising novel *B. burgdorferi* polypeptides are constructed comprising B cell and/or T cell epitopes from multiple serotypic variants of *B. burgdorferi*, each variant differing from another with respect to the locations or sequences of the epitopes within the polypeptide. In a more preferred embodiment, fusion proteins are constructed which comprise one or more of the novel *B. burgdorferi* polypeptides fused to other immunogenic *B. burgdorferi* polypeptides. Such fusion proteins are particularly effective in the prevention, treatment and diagnosis of Lyme disease as caused by a wide spectrum of *B. burgdorferi* isolates.

In another preferred embodiment of this invention, the novel *B. burgdorferi* polypeptides are fused to moieties, such as immunoglobulin domains, which may increase the stability and prolong the in vivo plasma half-life of the polypeptide. Such fusions may be prepared according to methods well known to those of skill in the art, for example, in accordance with the teachings of U.S. Pat. No. 4,946,778, or U.S. Pat. No. 5,116,964. The exact site of the fusion is not critical as long as the polypeptide retains the desired biological activity. Such determinations may be made according to the teachings herein or by other methods known to those of skill in the art.

It is preferred that the fusion proteins comprising the novel *B. burgdorferi* polypeptides be produced at the DNA level, e.g., by constructing a nucleic acid molecule encoding the fusion, transforming host cells with the molecule, inducing the cells to express the fusion protein, and recovering the fusion protein from the cell culture. Alternatively, the fusion proteins may be produced after gene expression according to known methods.

The novel *B. burgdorferi* polypeptides may also be part of larger multimeric molecules which may be produced recombinantly or may be synthesized chemically. Such multimers may also include the polypeptides fused or coupled to moieties other than amino acids, including lipids and carbohydrates.

Preferably, the multimeric proteins will consist of multiple T or B cell epitopes or combinations thereof repeated within the same molecule, either randomly, or with spacers (amino acid or otherwise) between them.

In the most preferred embodiment of this invention, the novel *B. burgdorferi* polypeptides of this invention which are also immunogenic *B. burgdorferi* polypeptides are incorporated into a multicomponent vaccine which also comprises other immunogenic *B. burgdorferi* polypeptides. Such a multicomponent vaccine, by virtue of its ability to elicit antibodies to a variety of immunogenic *B. burgdorferi* polypeptides, will be effective to protect against Lyme disease as caused by a broad spectrum of different *B. burgdorferi* isolates, even those that may not express one or more of the Osp proteins.

The multicomponent vaccine may contain the novel *B. burgdorferi* polypeptides as part of a multimeric molecule in which the various components are covalently associated. Alternatively, it may contain multiple individual components. For example, a multicomponent vaccine may be prepared comprising two or more of the novel *B. burgdorferi* polypeptides, or comprising one novel *B. burgdorferi* polypeptide and one previously identified *B. burgdorferi* polypeptide, wherein each polypeptide is expressed and purified from independent cell cultures and the polypeptides are combined prior to or during formulation.

Alternatively, a multicomponent vaccine may be prepared from heterodimers or tetramers wherein the polypeptides have been fused to immunoglobulin chains or portions thereof. Such a vaccine could comprise, for example, an OspF polypeptide fused to an immunoglobulin heavy chain and an OspA polypeptide fused to an immunoglobulin light chain, and could be produced by transforming a host cell with DNA encoding the heavy chain fusion and DNA encoding the light chain fusion. One of skill in the art will understand that the host cell selected should be capable of assembling the two chains appropriately. Alternatively, the heavy and light chain fusions could be produced from separate cell lines and allowed to associate after purification.

The desirability of including a particular component-and the relative proportions of each component may be determined by using the assay systems disclosed herein, or by using other systems known to those in the art. Most preferably, the multicomponent vaccine will comprise numerous T cell and B cell epitopes of immunogenic *B. burgdorferi* polypeptides, including the novel *B. burgdorferi* polypeptides of this invention.

This invention also contemplates that the novel *B. burgdorferi* polypeptides of this invention, either alone or with other immunogenic *B. burgdorferi* polypeptides, may be administered to an animal via a liposome delivery system in order to enhance their stability and/or immunogenicity. Delivery of the novel *B. burgdorferi* polypeptides via liposomes may be particularly advantageous because the liposome may be internalized by phagocytic cells in the treated animal. Such cells, upon ingesting the liposome, would digest the liposomal membrane and subsequently present the polypeptides to the immune system in conjunction with other molecules required to elicit a strong immune response.

The liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154. In addition, it may be desirable to express the novel *B. burgdorferi* polypeptides of this invention, as well as other selected *B. burgdorferi* polypeptides, as lipoproteins, in order to enhance their binding to liposomes.

Any of the novel *B. burgdorferi* polypeptides of this invention may be used in the form of a pharmaceutically acceptable salt. Suitable acids and bases which are capable of forming salts with the polypeptides of the present invention are well known to those of skill in the art, and include inorganic and organic acids and bases.

According to this invention, we describe a method which comprises the steps of treating an animal with a therapeutically effective amount of a novel *B. burgdorferi* polypeptide, or a fusion protein or a multimeric protein comprising a novel *B. burgdorferi* polypeptide, in a manner sufficient to prevent or lessen the severity, for some period of time, of *B. burgdorferi* infection. The polypeptides that are preferred for use in such methods are those that contain protective epitopes. Such protective epitopes may be B cell epitopes, T cell epitopes, or combinations thereof.

According to another embodiment of this invention, we describe a method which comprises the steps of treating an animal with a multicomponent vaccine comprising a therapeutically effective amount of a novel *B. burgdorferi* polypeptide, or a fusion protein or multimeric protein comprising such polypeptide in a manner sufficient to prevent or lessen the severity, for some period of time, of *B. burgdorferi* infection. Again, the polypeptides, fusion proteins and multimeric proteins that are preferred for use in such methods are those that contain protective epitopes, which may be B cell epitopes, T cell epitopes, or combinations thereof.

The most preferred polypeptides, fusion proteins and multimeric proteins for use in these compositions and methods are those containing both strong T cell and B cell epitopes. Without being bound by theory, we believe that this is the best way to stimulate high titer antibodies that are effective to neutralize *B. burgdorferi* infection. Such preferred polypeptides will be internalized by B cells expressing surface immunoglobulin that recognizes the B cell epitope(s). The B cells will then process the antigen and present it to T cells. The T cells will recognize the T cell epitope(s) and respond by proliferating and producing lymphokines which in turn cause B cells to differentiate into antibody producing plasma cells. Thus, in this system, a closed autocatalytic circuit exists which will result in the amplification of both B and T cell responses, leading ultimately to production of a strong immune response which includes high titer antibodies against the novel *B. burgdorferi* polypeptide.

One of skill in the art will also understand that it may be advantageous to administer the novel *B. burgdorferi* polypeptides of this invention in a form that will favor the production of T-helper cells type 2 ($T_H2$), which help B cells to generate antibody responses. Aside from administering epitopes which are strong B cell epitopes, the induction of $T_H2$ cells may also be favored by the mode of administration of the polypeptide for example by administering in certain doses or with particular adjuvants and immunomodulators, for example with interleukin-4.

To prepare the preferred polypeptides of this invention, in one embodiment, overlapping fragments of the novel *B. burgdorferi* polypeptides of this invention are constructed. The polypeptides that contain B cell epitopes may be identified in a variety of ways for example by their ability to (1) remove protective antibodies from polyclonal antiserum directed against the polypeptide or (2) elicit an immune response which is effective to prevent or lessen the severity of *B. burgdorferi* infection.

Alternatively, the polypeptides may be used to produce monoclonal antibodies which could be screened for their ability to confer protection against *B. burgdorferi* infection when used to immunize naive animals. Once a given monoclonal antibody is found to confer protection, the particular epitope that is recognized by that antibody may then be identified.

As recognition of T cell epitopes is MHC restricted, the polypeptides that contain T cell epitopes may be identified in vitro by testing them for their ability to stimulate proliferation and/or cytokine production by T cell clones generated from humans of various HLA types, from the lymph nodes of C3H/He mice, or from domestic animals. Compositions comprising multiple T cell epitopes recognized by individuals with different Class II antigens are useful for prevention and treatment of Lyme disease in a broad spectrum of patients.

In a preferred embodiment of the present invention, a novel *B. burgdorferi* polypeptide containing a B cell epitope is fused to one or more other immunogenic *B. burgdorferi* polypeptides containing strong T cell epitopes. The fusion protein that carries both strong T cell and B cell epitopes is able to participate in elicitation of a high titer antibody response effective to neutralize infection with *B. burgdorferi*.

Strong T cell epitopes may also be provided by non-*B. burgdorferi* molecules. For example, strong T cell epitopes have been observed in hepatitis B virus core antigen (HBcAg). Furthermore, it has been shown that linkage of one of these segments to segments of the surface antigen of Hepatitis B virus, which are poorly recognized by T cells, results in a major amplification of the anti-HBV surface antigen response, [D. R. Milich et al., "Antibody Production To The Nucleocapsid And Envelope Of The Hepatitis B Virus Primed By A Single Synthetic T Cell Site", Nature, 329, pp. 547–49 (1987)].

Therefore, in yet another preferred embodiment, B cell epitopes of the novel B. burgdorferi polypeptides are fused to segments of HBcAG or to other antigens which contain strong T cell epitopes, to produce a fusion protein that can elicit a high titer antibody response against B. burgdorferi. In addition, it may be particularly advantageous to link a novel B. burgdorferi polypeptide of this invention to a strong immunogen that is also widely recognized, for example tetanus toxoid.

It will be readily appreciated by one of ordinary skill in the art that the novel B. burgdorferi polypeptides of this invention, as well as fusion proteins and multimeric proteins containing them, may be prepared by recombinant means, chemical means, or combinations thereof.

For example, the polypeptides may be generated by recombinant means using the DNA sequences of B. burgdorferi strain N40 as set forth in the sequence listings contained herein. DNA encoding serotypic variants of the polypeptides may likewise be cloned, e.g., using PCR and oligonucleotide primers derived from the sequences herein disclosed.

In this regard, it may be particularly desirable to isolate the genes encoding novel B. burgdorferi polypeptides from strain 25015 and other strains of B. burgdorferi that are known to differ antigenically from strain N40, in order to obtain a broad spectrum of different epitopes which would be useful in the methods and compositions of this invention. For example, the OspA gene of B. burgdorferi strain 25015 is known to differ from the OspA gene of B. burgdorferi strain N40 to the extent that anti-OspA antibodies, which protect against subsequent infection with strain N40, appear ineffective to protect against infection with strain 25015.

Oligonucleotide primers and other nucleic acid probes derived from the genes encoding the novel B. burgdorferi polypeptides may also be used to isolate and clone other related surface proteins from B. burgdorferi and related spirochetes which may contain regions of DNA sequence homologous to the DNA sequences of this invention. In addition, the DNA sequences of this invention may also be used in PCR reactions to detect the presence of B. burgdorferi in a suspected infected sample.

If the novel B. burgdorferi polypeptides of this invention are produced recombinantly, they may be expressed in unicellular hosts. As is well known to one of skill in the art, in order to obtain high expression levels of foreign DNA sequences in a host, the sequences are generally operatively linked to transcriptional and translational expression control sequences that are functional in the chosen host. Preferably, the expression control sequences, and the gene of interest, will be contained in an expression vector that further comprises a selection marker.

The DNA sequences encoding the polypeptides of this invention may or may not encode a signal sequence. If the expression host is eukaryotic, it generally is preferred that a signal sequence be encoded so that the mature protein is secreted from the eukaryotic host.

An amino terminal methionine may or may not be present on the expressed polypeptides of this invention. If the terminal methionine is not cleaved by the expression host, it may, if desired, be chemically removed by standard techniques.

A wide variety of expression host/vector combinations may be employed in expressing the DNA sequences of this invention. Useful expression vectors for eukaryotic hosts, include, for example, vectors comprising expression control sequences from SV40, bovine papilloma virus, adenovirus, adeno-associated virus, cytomegalovirus and retroviruses. Useful expression vectors for bacterial hosts include bacterial plasmids, such as those from E. coli, including pBluescript, pGEX-2T, pUC vectors, col E1, pCR1, pBR322, pMB9 and their derivatives, wider host range plasmids, such as RP4, phage DNAS, e.g., the numerous derivatives of phage lambda, e.g. $\lambda$GT10 and $\lambda$GT11, and other phages. Useful expression vectors for yeast cells include the $2\mu$ plasmid and derivatives thereof. Useful vectors for insect cells include pVL 941.

In addition, any of a wide variety of expression control sequences—sequences that control the expression of a DNA sequence when operatively linked to it—may be used in these vectors to express the DNA sequences of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast $\alpha$-mating system and other constitutive and inducible promoter sequences known to control the expression of genes of prokaryotic or eukaryotic cells or their viruses, and various combinations thereof.

In a preferred embodiment, DNA sequences encoding the novel B. burgdorferi polypeptides of this invention are cloned in the expression vector lambda ZAP II (Stratagene, La Jolla, Calif.), in which expression from the lac promoter may be induced by IPTG.

In another preferred embodiment, DNA encoding the novel B. burgdorferi polypeptides of this invention is inserted in frame into an expression vector that allows high level expression of the polypeptide as a glutathione S-transferase fusion protein. Such a fusion protein thus contains amino acids encoded by the vector sequences as well as amino acids of the novel B. burgdorferi polypeptide.

A wide variety of unicellular host cells are useful in expressing the DNA sequences of this invention. These hosts may include well known eukaryotic and prokaryotic hosts, such as strains of E. coli, Pseudomonas, Bacillus, streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, and human cells, as well as plant cells in tissue culture.

It should of course be understood that not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the sequence, its controllability, and its compatibility with the DNA sequence of this invention, particularly with regard to potential secondary structures. Unicellular hosts should be selected by consideration of their compatibility with the chosen vector, the toxicity of the product coded for by the DNA sequences of this invention, their secretion characteristics, their ability to fold the polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention on fermentation or in other large scale cultures.

The molecules comprising the novel *B. burgdorferi* polypeptides encoded by the DNA sequences of this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

In addition, the novel *B. burgdorferi* polypeptides may be generated by any of several chemical techniques. For example, they may be prepared using the solid-phase synthetic technique originally described by R. B. Merrifield, "Solid Phase Peptide Synthesis. I. The Synthesis Of A Tetrapeptide", *J. Am. Chem. Soc.*, 83, p. 2149–54 (1963), or they may be prepared by synthesis in solution. A summary of peptide synthesis techniques may be found in E. Gross & H. J. Meinhofer, 4 The Peptides: Analysis, Synthesis, Biology; Modern Techniques Of Peptide And Amino Acid Analysis, John Wiley & Sons, (1981) and M. Bodanszky, Principles of Peptide Synthesis, Springer-Verlag (1984).

Typically, these synthetic methods comprise the sequential addition of one or more amino acid residues to a growing peptide chain. Often peptide coupling agents are used to facilitate this reaction. For a recitation of peptide coupling agents suitable for the uses described herein see M. Bodansky, supra. Normally, either the amino or carboxyl group of the first amino acid residue is protected by a suitable, selectively removable protecting group. A different protecting group is utilized for amino acids containing a reactive side group, e.g., lysine. A variety of protecting groups known in the field of peptide synthesis and recognized by conventional abbreviations therein, may be found in T. Greene, Protective Groups In Organic Synthesis, Academic Press (1981).

According to another embodiment of this invention, antibodies directed against the novel *B. burgdorferi* polypeptides are generated. Such antibodies are immunoglobulin molecules or portions thereof that are immunologically reactive with a novel *B. burgdorferi* polypeptide of the present invention. It should be understood that the antibodies of this invention include antibodies immunologically reactive with fusion proteins and multimeric proteins comprising a novel *B. burgdorferi* polypeptide.

Antibodies directed against a novel *B. burgdorferi* polypeptide may be generated by infection of a mammalian host with *B. burgdorferi*, or by immunization of a mammalian host with a novel *B. burgdorferi* polypeptide of the present invention. Such antibodies may be polyclonal or monoclonal, it is preferred that they are monoclonal. Methods to produce polyclonal and monoclonal antibodies are well known to those of skill in the art. For a review of such methods, see Antibodies, A Laboratory Manual, supra, and D. E. Yelton, et al., Ann. Rev. of Biochem., 50, pp. 657–80 (1981). Determination of immunoreactivity with a novel *B. burgdorferi* polypeptide of this invention may be made by any of several methods well known in the art, including by immunoblot assay and ELISA.

An antibody of this invention may also be a hybrid molecule formed from immunoglobulin sequences from different species (e.g., mouse and human) or from portions of immunoglobulin light and heavy chain sequences from the same species. It may be a molecule that has multiple binding specificities, such as a bifunctional antibody prepared by any one of a number of techniques known to those of skill in the art including: the production of hybrid hybridomas; disulfide exchange; chemical cross-linking; addition of peptide linkers between two monoclonal antibodies; the introduction of two sets of immunoglobulin heavy and light chains into a particular cell line; and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes.

In addition, it may be advantageous to couple the antibodies of this invention to toxins such as diphtheria, pseudomonas exotoxin, ricin A chain, gelonin, etc., or antibiotics such as penicillins, tetracyclines and chloramphenicol.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Antibodies directed against a novel *B. burgdorferi* polypeptide may be used in compositions and methods for the prevention and treatment of Lyme disease as caused by infection with *B. burgdorferi*. For example, we demonstrate herein that the level of *B. burgdorferi* in infected ticks is decreased by allowing them to feed on the blood of animals immunized with OspE and OspF polypeptides. This decrease is likely due to exposure of the spirochetes in the ticks to anti-OspE and anti-OspF antibodies present in the blood of the immunized animals.

Accordingly, it is clear that such antibodies have utility in therapeutic and prophylactic compositions and methods directed against Lyme disease and *B. burgdorferi* infection.

The antibodies of this invention also have a variety of other uses. For example, they are useful as reagents to screen for expression of the *B. burgdorferi* polypeptides, either in libraries-constructed from-*B. burgdorferi* DNA or from other samples in which the proteins may be present. Moreover, by virtue of their specific binding affinities, the antibodies of this invention are also useful to purify or remove polypeptides from a given sample, to block or bind to specific epitopes on the polypeptides and to direct various molecules, such as toxins, to the surface of *B. burgdorferi*.

To screen the novel *B. burgdorferi* polypeptides and antibodies of this invention for their ability to confer protection against Lyme disease or their ability to lessen the severity of *B. burgdorferi* infection, C3H/He mice are preferred as an animal model of course, while any animal that is susceptible to infection with *B. burgdorferi* may be useful, C3H/He mice are not only susceptible to *B. burgdorferi* infection but are also afflicted with clinical symptoms of a disease that is remarkably similar to Lyme disease in humans. Thus, by administering a particular polypeptide or antibody to C3H/He mice, one of skill in the art may determine without undue experimentation whether that polypeptide or antibody would be useful in the methods and compositions claimed herein.

The administration of the novel *B. burgdorferi* polypeptide or antibody of this invention to the animal may be accomplished by any of the methods disclosed herein or by a variety of other standard procedures. For a detailed discussion of such techniques, see Antibodies, A Laboratory Manual, supra. Preferably, if a polvpeptide is used, it will be administered with a pharmaceutically acceptable adjuvant, such as complete or incomplete Freund's adjuvant, RIBI (muramyl dipeptides) or ISCOM (immunostimulating complexes). Such adjuvants may protect the polypeptide from rapid dispersal by sequestering it in 3.0 a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Once the novel *B. burgdorferi* polypeptides or antibodies of this invention have been determined to be effective in the screening process, they may then be used in a therapeutically effective amount in pharmaceutical compositions and methods to treat or prevent Lyme disease which may occur naturally in various animals.

The pharmaceutical compositions of this invention may be in a variety of conventional depot forms. These include, for example, solid, semi-solid and liquid dosage forms, such as tablets, pills, powders, liquid solutions or suspensions, liposomes, capsules, suppositories, injectable and infusible solutions. The preferred form depends upon the intended mode of administration and prophylactic application.

Such dosage forms may include pharmaceutically acceptable carriers and adjuvants which are known to those of skill in the art. These carriers and adjuvants include, for example, RIBI, ISCOM, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica,-magnesium trisilicate, polyvinyl pyrrolidone, cellulose-based substances, and polyethylene glycol. Adjuvants for topical or gel base forms may be selected from the group consisting of sodium carboxymethylcellulose, polyacrylates, polyoxyethylene-polyoxypropylene-block polymers, polyethylene glycol, and wood wax alcohols.

The vaccines and compositions of this invention may also include other components or be subject to other treatments during preparation to enhance their immunogenic character or to improve their tolerance in patients.

Compositions comprising an antibody of this invention may be administered by a variety of dosage forms and regimens similar to those used for other passive immunotherapies and well known to those of skill in the art. Generally, the novel *B. burgdorferi* polypeptides may be formulated and administered to the patient using methods and compositions similar to those employed for other pharmaceutically important polypeptides (e.g., the vaccine against hepatitis).

Any pharmaceutically acceptable dosage route, including parenteral, intravenous, intramuscular, intralesional or subcutaneous injection, may be used to administer the polypeptide or antibody composition. For example, the composition may be administered to the patient in any pharmaceutically acceptable dosage form including those which may be administered to a patient intravenously as bolus or by continued infusion over a period of hours, days, weeks or months, intramuscularly—including paravertebrally and periarticularly—subcutaneously, intracutaneously, intraarticularly, intrasynovially, intrathecally, intralesionally, periostally or by oral or topical routes. Preferably, the compositions of the invention are in the form of a unit dose and will usually be administered to the patient intramuscularly.

The novel *B. burgdorferi* polypeptides or antibodies of this invention may be administered to the patient at one time or over a series of treatments. The most effective mode of administration and dosage regimen will depend upon the level of immunogenicity, the particular composition and/or adjuvant used for treatment, the severity and course of the expected infection, previous therapy, the patient's health status and response to immunization, and the judgment of the treating physician. For example, in an immunocompetent patient, the more highly immunogenic the polypeptide, the lower the dosage and necessary number of immunizations. Similarly, the dosage and necessary treatment time will be lowered if the polypeptide is administered with an adjuvant. Generally, the dosage will consist of 10 $\mu$g to 100 mg of the purified polypeptide, and preferably, the dosage will consist of 100–1000 $\mu$g. Generally, the dosage for an antibody will be 0.5 mg–3.0 g.

In a preferred embodiment of this invention, the novel *B. burgdorferi* polypeptide is administered with an adjuvant, in order to increase its immunogenicity. Useful adjuvants include RIBI, and ISCOM, simple metal salts such as aluminum hydroxide, and oil based adjuvants such as. complete and incomplete Freund's adjuvant. When an oil based-adjuvant is used, the polypeptide usually is administered in an emulsion with the adjuvant.

In yet another preferred embodiment, *E. coli* expressing proteins comprising a novel *B. burgdorferi* polypeptide are administered orally to non-human animals to decrease or lessen the severity of *B. burgdorferi* infection. For example, a palatable regimen of bacteria expressing a novel *B. burgdorferi* polypeptide, alone or in the form of a fusion protein or multimeric protein, may be administered with animal food to be consumed by wild mice or deer, or by domestic animals. Ingestion of such bacteria may induce an immune response comprising both humoral and cell-mediated components. See J. C. Sadoff et al., "Oral Salmonella Typhimurium Vaccine Expressing Circumsporozoite Protein Protects Against Malaria", *Science*, 240, pp. 336–38 (1988) and K. S. Kim et al., "Immunization Of Chickens With Live *Escherichia coli* Expressing Eimeria acervulina Merozoite Recombinant Antigen Induces Partial Protection Against Coccidiosis", *Inf. Immun.*, 57, pp. 2434–40 (1989). Moreover, the level of *B. burgdorferi* infection in ticks feeding on such animals will be lessened or eliminated, thus inhibiting transmission to the next animal.

According to yet another embodiment, the antibodies of this invention as well as the novel *B. burgdorferi* polypeptides of this invention, and the DNA sequences encoding them are useful as diagnostic agents for detecting infection with *B. burgdorferi*, because the polypeptides are capable of binding to antibody molecules produced in animals, including humans that are infected with *B. burgdorferi*, and the antibodies are capable of binding to *B. burgdorferi* or antigens thereof.

Such diagnostic agents may be included in a kit which may also comprise instructions for use and other appropriate reagents, preferably a means for detecting when the polypeptide or antibody is bound. For example, the polypeptide or antibody may be labeled with a detection means that allows for the detection of the polypeptide when it is bound to an antibody, or for the detection of the antibody when it is bound to *B. burgdorferi* or an antigen thereof.

The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}$I or $^{51}$Cr that produces gamma ray emissions, or a radioactive element that emits positrons which produce gamma rays upon encounters with electrons present in the test solution, such as $^{11}$C, $^{15}$O, or $^{13}$N. Binding may also be detected by other methods, for example via avidin-biotin complexes.

The linking of the detection means is well known in the art. For instance, monoclonal antibody molecules produced by a hybridoma can be metabolically labeled by incorporation of radioisotope-containing amino acids in the culture medium, or polypeptides may be conjugated or coupled to a detection means through activated functional groups.

The diagnostic kits of the present invention may be used to detect the presence of a quantity of *B. burgdorferi* or anti-*B. burgdorferi* antibodies in a body fluid sample such as serum, plasma or urine. Thus, in preferred embodiments, a novel *B. burgdorferi* polypeptide or an antibody of the present invention is bound to a solid support typically by adsorption from an aqueous medium. Useful solid matrices are well known in the art, and include crosslinked dextran; agarose; polystyrene; polyvinylchloride; cross-linked polyacrylamide; nitrocellulose or nylon-based materials; tubes., plates or the wells of microtiter plates. The polypeptides or antibodies of the present invention may be used as diagnostic agents in solution form or as a substantially dry powder, e.g., in lyophilized form.

Novel *B. burgdorferi* polypeptides and antibodies directed against those polypeptides provide much more specific diagnostic reagents than whole *B. burgdorferi* and thus may alleviate such pitfalls as false positive and false negative results.

One skilled in the art will realize that it may also be advantageous in the preparation of detection reagents to utilize epitopes from other *B. burgdorferi* proteins, including the flagella-associated protein, and antibodies directed against such epitopes. As explained further in Example VI, infra, antibodies to OspF tend to occur late in the course of *B. burgdorferi* infection while antibodies against OspE tend to appear much earlier. Accordingly, it may be particularly advantageous to use OspF epitopes in combination with epitopes from other *B. burgdorferi* proteins, such as OspE and flagellin, that elicit antibodies that occur in the early stages of Lyme disease. Diagnostic reagents containing multiple epitopes which are reactive with antibodies appearing at different times are useful to detect the presence of anti-*B. burgdorferi* antibodies throughout the course of infection and to diagnose Lyme disease at all stages.

The polypeptides and antibodies of the present invention, and compositions and methods comprising them, may also be useful for detection, prevention, and treatment of other infections caused by spirochetes which may contain surface proteins sharing amino acid sequence or conformational similarities with the novel *B. burgdorferi* polypeptides of the present invention. These other spirochetes include Borrelia Hermsii and Borrelia Recurientis, Leptospira, and Treponema.

In order that this invention may be better understood, the following examples are set forth. These examples are for purposes of illustration only, and are not to be construed as limiting the scope of the invention in any manner.

EXAMPLE I

Construction and Screening of a *B. burgdorferi* Expression Library

We had a *B. burgdorferi* genomic DNA expression library constructed in Lambda ZAP II by Stratagene (La Jolla, Calif.) Briefly, we grew *B. burgdorferi* strain N40 in modified Barbour-Stoener-Kelly (BSK II) medium at 32° C. for 7 days, harvested by centrifugation at 16,000 rpm for 30 minutes, and lysed with SDS [A. G. Barbour, "Isolation and Cultivation of Lyme Disease Spirochetes", *Yale J. Biol. Med.*, 57, pp. 521–25 (1984)]. We then isolated the genomic DNA from the spirochetes and purified it by phenol/chloroform extraction.

To construct the library, 200 μg of DNA was randomly sheared, blunt-ended with S1 nuclease, and the EcoR1 sites were methylated with EcoR1 methylase. EcoR1 linkers were then ligated to the ends of the DNA molecules, the DNA was digested with EcoR1 and the fragments were purified over a sucrose gradient. Fragments of 1 to 9 kb were isolated and ligated to EcoR1 digested Lambda ZAP II arms.

We prepared *E. coli* SURE bacteria (Stratagene) for phage infection as follows. We picked a single colony into LB media supplemented with 0.2% maltose and 10 nM magnesium sulfate and cultured overnight at 30° C. with vigorous shaking. We then centrifuged the cells at 2000 rpm for 10 minutes and resuspended in 10 mM magnesium sulfate. The cells were further diluted to O.D.$_{600}$=0.5 for bacteriophage infection.

To screen the library, we used the picoBlue Immunoscreening Kit (Stratagene). We plated 10,000 plaque forming units of recombinant phage on a lawn of bacteria, induced protein expression with 10 mM IPTG and transferred the proteins to nitrocellulose filters according to methods well known in the art.

We prepared rabbit anti-*B. burgdorferi* N40 antiserum as follows. We injected rabbits with an inoculum of 1 ×10$^8$ live *B. burgdorferi* N40 in PBS via the marginal ear vein and boosted with the same dosage at 14, 21 and 49 days. Two weeks after the last boost, we sacrificed and bled the rabbits and separated the anti-*B. burgdorferi* antiserum by centrifuging the blood at 2000 rpm for 15 minutes.

To remove antibodies in the serum that would recognize *E. coli* and phage proteins, we absorbed the antiserum with an *E. coli* /phage lysate (Stratagene) as follows. We diluted the lysate 1:10 in Tris-buffered saline with 0.05% Tween-20 (TBST). We then incubated 0.45 μM pore size nitrocellulose filters (Millipore, Bedford, Mass.) in the lysate for 30 minutes at room temperature, removed and air dried the filters on Whatman filter paper (Whatman International Ltd., Maidstone, England), and washed 3 times (5 minutes each) with TBS. We blocked the filters by immersing in 1% Bovine Serum Albumin (BSA) in TBS for 1 hour at room temperature and rinsing 3 times with TBST. We then diluted the rabbit antiserum 1:5 in TBST, incubated it with the filters with shaking for 10 minutes at 37° C., and removed and discarded the filters.

After absorption, we diluted the antiserum to a final dilution of 1:200 and used it to screen the nitrocellulose filters containing the expressed proteins from the lambda ZAP library according to manufacturer's instructions. After washing, we incubated the filters with a 1:5000 dilution of alkaline phosphatase-conjugated goat anti-rabbit IgG antibody (Organon Teknika Corp., West Chester, Pa.), and used nitro blue tetrazolium (NBT) (Stratagene) and 5-bromo-4-chloro-3-indolyl phosphate (BCIP) (Stratagene) for color development.

Ten positive clones were originally identified. We screened each of these positive clones with OspA, OspB and flagellin DNA probes by Southern blotting and identified six clones that were not reactive with any of the probes. We excised the pBluescript plasmid from one of those clones by infection of XL1-Blue E. coli cells and rescue with R408 helper phage according to the manufacturer's instructions. We designated that plasmid "clone #11."

We analyzed the protein expression of clone #11 as follows. We grew the XL1-Blue cells containing clone #11 to $OD_{600}$=0.5 (about 3 hours) and then induced a portion of the cells with IPTG for about 2 hours. We then centrifuged the cells at 13,000 rpm for 1 minute and resuspended the pellet in 1/10 volume of PBS with 1% Triton S-100 and 1/10 volume of 2x sample buffer. After boiling for 5 minutes, we electrophoresed the sample through a 12% SDS polyacrylamide gel and transferred overnight to a nitrocellulose filter. We blocked the filters for 1 hour with blocking solution, incubated for 1 hour with combined mouse anti-OspE and anti-OspF anti-serum diluted 1:100, washed 3 times for 5 minutes with TBST and developed with NBT and BCIP. The mouse antiserum was prepared as set forth in Example V.

As shown in FIG. 1, the combined mouse antiserum bound to proteins having apparent molecular weights of 19 and 29 kDa in lysates from both IPTG induced (Lane 1) and uninduced (Lane 2) cultures of clone #11, suggesting those proteins were expressed from their own promoter sequences. Binding was absent in lysates from uninduced XL-1 Blue control cells (Lane 3).

EXAMPLE II

Seauence Analysis of the OspE-OspF Operon

We generated a nested set of deletions in the DNA insert of clone #11 with the Erase-A-Base System (Promega, Madison, Wis.) (using SmaI to generate the 5' blunt end and BstXI to generated 3' overhang). We then sequenced the subclones using the Sequenase Kit (United States Biochemical Corp., Cleveland, Ohio) and reconstructed the entire sequence using MacVector (International Biotechnology, Inc., New Haven, C.T). Analysis of the DNA sequence of the insert revealed that we had isolated a novel, bicistronic B. burgdorferi operon having the sequence set forth in SEQ ID NO: 1.

We designated the antigens encoded by the two genes in the operon as OspE and OspF. As shown in SEQ ID NO: 1, the OspE gene, at the 5' end of the operon, contains a 513 nucleotide open reading frame capable of encoding a 171-amino acid protein (SEQ ID NO: 2) with a calculated molecular weight of 19.2 kDa. The ATG start codon for the OspF gene is located 27 nucleotides downstream of the TAG stop codon of the OspE gene. The OspF gene contains an open reading frame of 690 nucleotides, capable of encoding a protein of 23U amino acids with a calculated molecular weight of 26.1 kDa (SEQ ID NO: 3). The TAA stop codon of the OspF gene is followed by a putative stem and loop structure with dyad symmetry.

A consensus ribosome binding site with the Shine-Dalgarno sequence is located 10 bp gupstream of the OspE ATG start codon. Further upstream of this translational initiation sequence are the promoter segments known as the "–10" region and the "–35" region, which are similar to those found in E. coli and other B. burgdorferi genes. (See FIG. 2 for a comparison of these regions between various B. burgdorferi genes). An additional ribosome binding site, consisting of a Shine-Dalgarno sequence preceded by an adenine is located 14 bp upstream of the ATG start codon of the OspF gene. The location of these sequence elements suggests that both the OspE and OspF genes are controlled by a single promoter.

Figure 5:
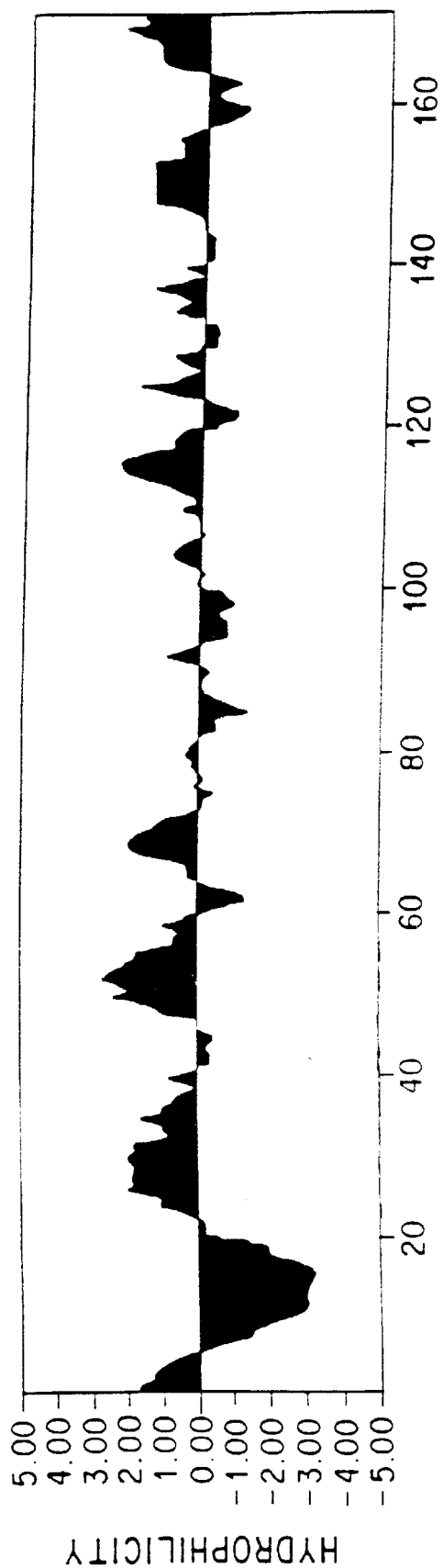
FIGS. 5 and 6 depict the hydrophilicity profiles of OspE and OspF, respectively, with a hydrophilicity window size of 7 and a Kyte-Doolittle hydrophilicity scale.
Figure 6:
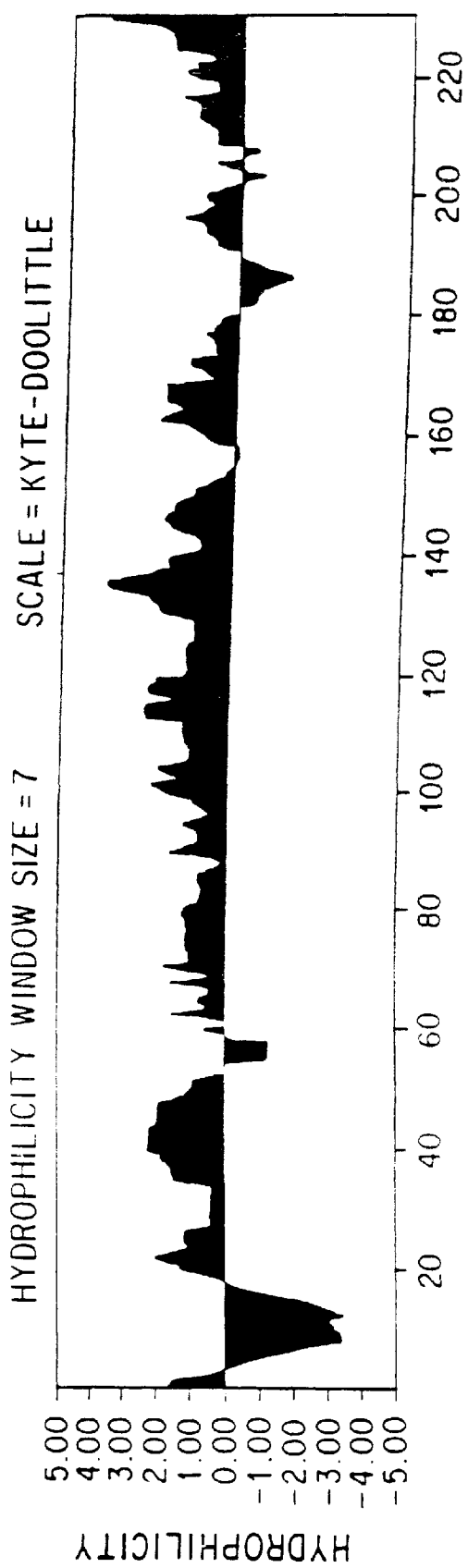

Both the OspE and OspF proteins have a comparatively high content of lysine and glutamic acid (FIG. 3). Other preferred codons are leucine, isoleucine, glycine and serine (FIG. 4), with the preferred nucleotide in the wobble position being an A or a U. On the basis of amino acid composition, we calculated the isoelectric point of OspE and OspF as 8.05 and 5.33, respectively. The hydrophilicity profiles of OspE and OspF, shown in FIG. 5 and 6, respectively, suggest that both are hydrophilic proteins.

Like OspA, OspB and OspD, the proteins encoded by the OspE and OspF genes appear to be surface lipoproteins. As shown in FIG. 7, each protein begins with a basic N-terminal peptide (amino acids 1–5 of SEQ ID NOS: 2 and 3, respectively) followed by an amino-terminal hydrophobic domain of about 20 amino acids that corresponds to the leader peptide found in typical prokaryotic lipoprotein precursors [M. E. Brandt et al., supra and C. H. Wu and M. Tokunaga, "Biogenesis of Lipoproteins in Bacteria", Current Tonics in Microbiology and Immunology, 125, pp. 127–157 (1986)].

The carboxyl terminus of the hydrophobic domain contains a cleavage site presumably recognized by a B. burgdorferi signal peptidase. In OspE, the potential. cleavage site is located between $Ala_{19}$ and $Cys_{20}$. In OspF, the potential cleavage site is located between $Ser_{17}$ and $Cys_{18}$.

The consensus sequence of typical bacterial lipoprotein precursors recognized and cleaved by signal peptidase II is a leucine and a cysteine separated by two, usually small, neutral, amino acids. [C. H. Wu et al., supra]. Indeed, in the OspA and OspB genes of B. burgdorferi B31, the intervening amino acids are isoleucine and alanine (OspA) or isoleucine and glycine (OspB) [S. Bergstrom et al., "Molecular Analysis of Linear Plasmid-Encoded Major Surface Proteins, OspA and OspB, of the Lyme Disease Spirochaete Borrelia burgdorferi," Mol. Microbiol., 3, 479–86 (1989)]. In contrast, as shown in FIG. 7, the signal sequences of the B. burgdorferi N40 OspE gene (amino acids 16–20 of SEQ ID NO: 2) and OspF gene (amino acids 14–18 of SEQ ID NO: 3), like the OspC-Pko and OspD-B31 genes, contain three amino acids between the leucine and cysteine instead of two (phenylalanine, isoleucine and serine in the case of OspC-Pko; serine, isoleucine and serine in the case of OspD-B31). (See R. S. Fuchs et al. and S. J. Norris et al., supra). However, despite this variation in the signal sequence, OspA, OspB and OspD have been shown to be lipoproteins by the established, [$^3$H]-palmitate labelling procedure. (See M. E. Brandt et al. and S. J. Norris et al., supra.) The leader signal sequences of OspE and OspF suggest that these surface proteins may be processed as lipoproteins as well. The addition of a lipid moiety at the cysteine residue could serve to anchor the proteins to the outer surface of the spirochetes (see H. C. Wu and M. Tokunaga, supra).

Finally, both OspE and OspF contain long hydrophilic domains separated by short stretches of hydrophobic segments. However, while the first 30 amino acids of OspE and OspF share a 60% homology in amino acid sequence (see FIG. 7), beyond that N-terminal region, no significant homology was noted.

EXAMPLE III

Mapping of the OspE-OspF Operon

Figure 8:
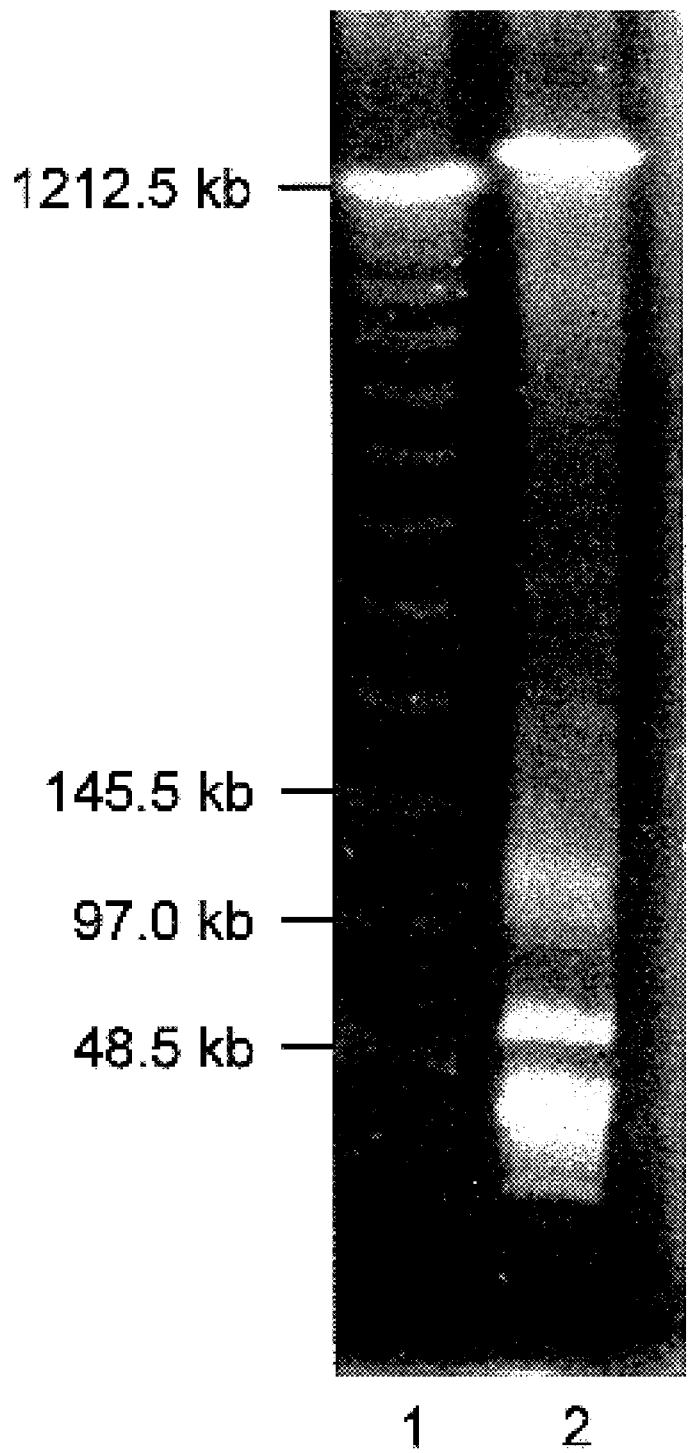
FIG. 8 depicts the separation of *B. burgdorferi* plasmid and chromosomal DNA by pulsed-field gel electrophoresis. The gel was visualized by staining with ethidium bromide. Lane 1 contains the molecular weight standard (concatemers of phage λ), lane 2 contains *B. burgdorferi* DNA.

We mapped the OspE-OspF operon by pulsed-field electrophoresis with total *B. burgdorferi* N40 DNA using a modification of the technique described in M.S. Ferdows and A. G. Barbour, "Megabase-Sized Linear DNA in the Bacterium *Borrelia burgdorferi*, the Lyme Disease Agent", *Proc. Natl. Acad. Sci.*, 86, pp. 5969–5973 (1989). Briefly, we separated the chromosomal and plasmid DNA by loading DNA plugs containing approximately $10^8$ *B. burgdorferi* N40 onto a 0.8% agarose gel. We electrophoresed the DNA in TBE buffer using the Chef-DRII system (Bio-Rad Laboratories, Richmond, Calif.) at 14° C. for 18 hours at 198V, with ramped pulse times from 1 to 30 sec. As shown in FIG. 8, the chromosomal band of *B. burgdorferi* N40 DNA migrates slightly slower than the 1212.5 kb marker, indicating it may be larger than previously described (1000 kb). Plasmids can be seen clearly at molecular weights of 49 kb and lower.

After Southern blotting, we hybridized the *B. burgdorferi* DNA with PCR-amplified radiolabelled OspE and OspF DNA sequences. To prepare the amplified OspE DNA, we used oligonucleotide primers having the sequences set forth in SEQ ID NO: 8 and 9. To prepare the amplified OspF DNA, we used oligonucleotide-primers having the sequences set forth in SEQ ID NO: 10 and 11. We used OspA and OspD probes as controls in the Southern blot.

Figure 9:
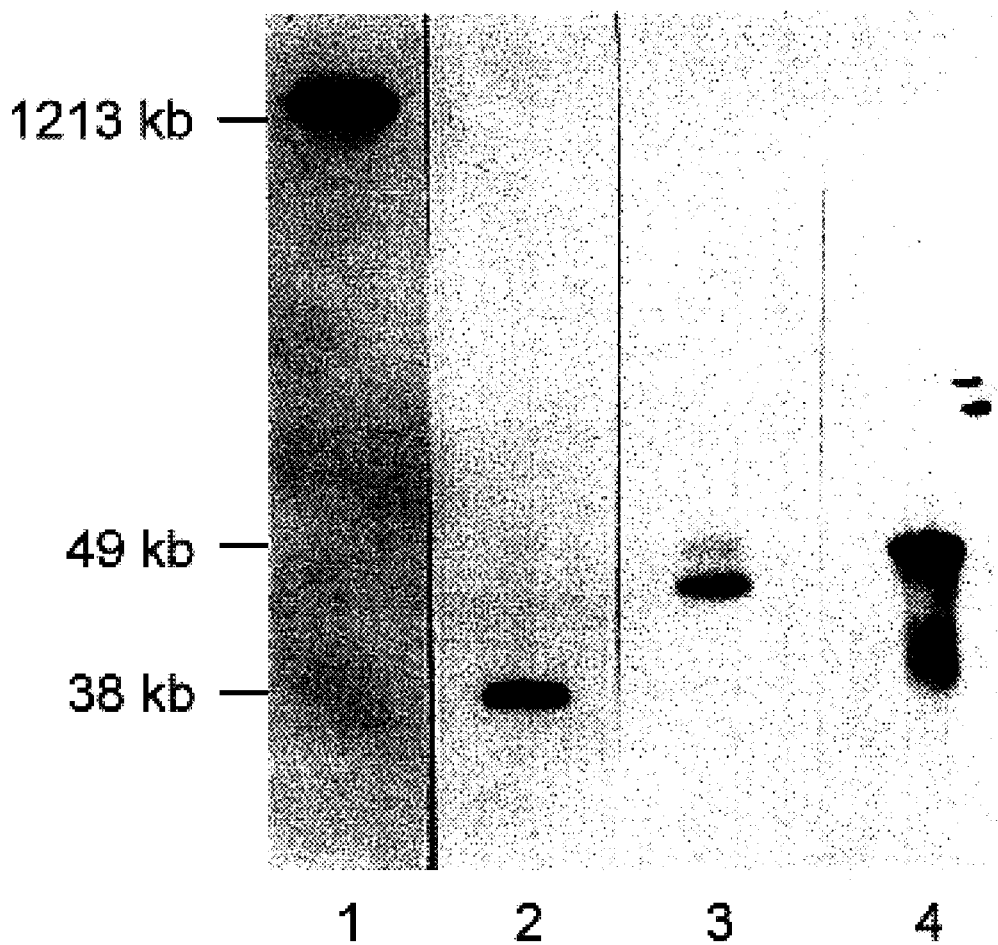
FIG. 9 depicts Southern blots of several lanes of *B. burgdorferi* DNA separated by pulsed-field gel electrophoresis and hybridized with various *B. burgdorferi* probes. Lane 1 is hybridized with a flagellin probe, lane 2 with an OspD probe, lane 3 with an OspF probe and lane 4 with an OspA probe.

As expected, the OspA and OspD probes hybridized to plasmids migrating at 49 kb and 38 kb, respectively [A. G. Barbour and C. F. Garon, "Linear Plasmids of the Bacterium *Borrelia burgdorferi* Have Covalently Closed Ends", Science, 237, pp. 409–411 (1987) and S. J. Norris et al., supra] (See FIG. 9). The OspF probe bound to a plasmid which appeared to migrate at the same molecular weight as a linear plasmid of around 45 kb (FIG. 9, lane 3) and also showed some weak binding to the 49 kb plasmid or a comigrating plasmid. The OspE probe also bound to the 45 kb plasmid (data not shown).

EXAMPLE IV

Expression of OspE and OspF Polypeptides

In order to express the OspE and OspF genes, we utilized the pMX vector, which is capable of directing expression of cloned inserts as glutathione S-transferase fusion proteins [see J. Sears et al., "Molecular Mapping of OspA-Mediated Immunity to Lyme Borreliosis", *J. Immunol.*, 147, pp. 1995–2000 (1991)]. We first used PCR to amplify OspE and OspF genes lacking the sequences encoding the hydrophobic leader peptides. We chose to delete those sequences to ensure that OspE and OspF would be expressed as soluble fusion proteins rather than as lipoproteins, which would be anchored to the cell membrane.

To amplify the OspE gene, we selected the primers shown in SEQ ID NO: 8 and 9. These primers allow amplification of a DNA sequence encoding amino acids 21–171 of SEQ ID NO: 2, flanked by a BamH1 site on the 5' end and an Xho I site on the 3' end. The primers we used to amplify the OspF gene, shown in SEQ ID NO: 10 and 11, result in amplification of a DNA sequence encoding amino acids 19–230 of SEQ ID NO: 3, flanked by an EcoR1 site on the 5' end and an Xho I site on the 3'end. The amplification was conducted for 30 cycles with initial template denaturation at 94° C. for 1 minute, annealing at 40' C. for 2 minutes and extension at 72° C. for 3 minutes.

We then ligated the amplified sequences to appropriately digested pMX vector and transformed DH5 α*E. coli* according to methods well known to those of skill in the art. After selecting subclones containing the desired inserts, we cultured the cells and induced expression of the OspE and OspF genes as glutathione S-transferase fusion proteins.

Figure 10:
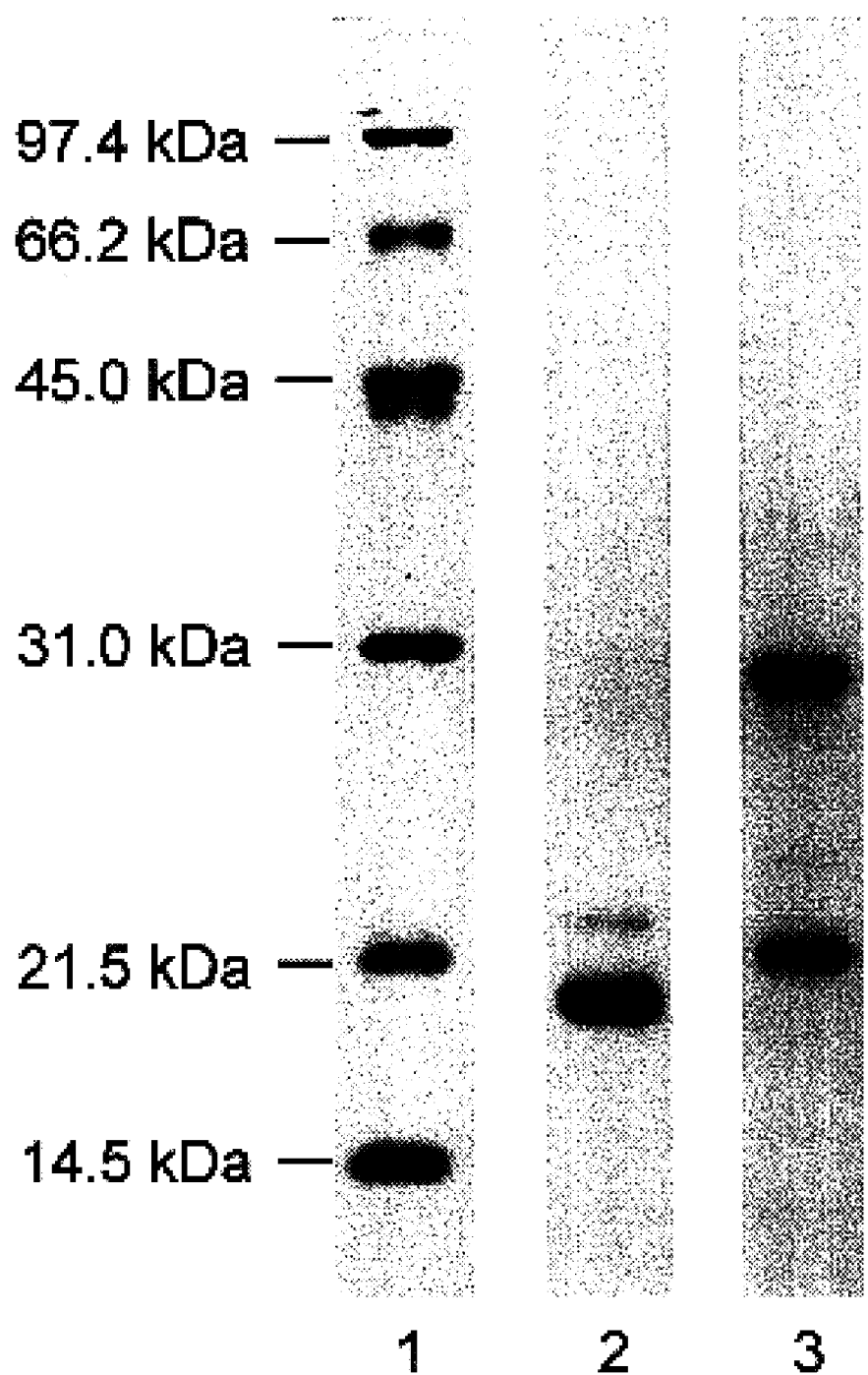
FIG. 10 depicts an SDS-PAGE-gel of purified Δ20-OspE and Δ18-OspF polypeptides. Lane 1 contains molecular weight markers, lane 2 contains Δ20-OspE polypeptide and lane 3 contains Δ18-OspF polypeptide.

We purified the glutathione S-transferase OspE and OspF fusion proteins (GT-OspE and GT-OspF, respectively) from cell lysates using a glutathione-Sepharose 4B column (Pharmacia) according to the manufacturer's instructions. In addition, we purified the OspE and OspF proteins without the glutathione S-transferase sequences as follows. We loaded the OspE and OspF glutathione S-transferase fusion proteins over the glutathione-Sepharose 4B column, added 25 units of thrombin and incubated overnight at room temperature. We then eluted the proteins with 50 mM Tris-$CaCl_2$-NaCl, treated the eluent with anti-thrombin beads for 1.5 to 2 hours and centrifuged at 13,000 rpm. The purified recombinant OspE (Δ20-OspE) and OspF (Δ18-OspF) polypeptides obtained from this procedure are shown in lanes 2 and 3, of FIG. 10, respectively.

EXAMPLE V

Preparation of Anti-OspE and Anti-OspF Antibodies

To determine whether OspE or OspF polypeptides were capable of eliciting an immune response, we immunized C3H/HeJ mice (Jackson Laboratory, Bar Harbor, Me.) subcutaneously with 10 micrograms of-either GT-OspE, GT-OspF, Δ20-OspE or Δ18-OspF in complete Freund's adjuvant and boosted with the same amount in incomplete Freund's adjuvant at 14 and 28 days. Control mice were immunized in the same manner with either recombinant glutathione S-transferase or bovine serum albumin (BSA). We also immunized white New Zealand rabbits (Millbrook, Amherst, Mass.) in a similar fashion with 50 micrograms of either Δ20-OspE or Δ18-OspF to obtain antisera for immunofluorescence studies.

Ten days after the last boost, we collected sera from the immunized animals and used it to hybridize to Western blots of SDS-PAGE gels of *B. burgdorferi* N40 extract or various of the recombinant polypeptides. We detected binding with a 1:5200 dilution of alkaline phosphatase-labeled goat anti-mouse immunoglobulin G and developed with nitroblue tetrazolium and 5-bromo-4-chloro-indolyl phosphate. Alternatively, we used the ECL kit (Amersham, Arlington Heights, Ill.) in which the secondary antibody, horseradish peroxidase-labeled goat anti-mouse IgG, can be detected at a dilution of 1:4000.

All of the OspE and OspF immunogens elicited antibodies in mice that were detectable by immunoblotting at a dilution of 1:5000. Similarly, Δ20-OspE and Δ18-OspF elicited antibodies in the immunized rabbits that were detectable by immunoblotting at a dilution of 1:1000. We note that the relatively low antibody titers suggest that the recombinant OspE and OspF molecules used are not particularly immunogenic. For example, immunization with GT-OspA elicited a titer in rabbits of 1:10,000,000.

Figure 11:
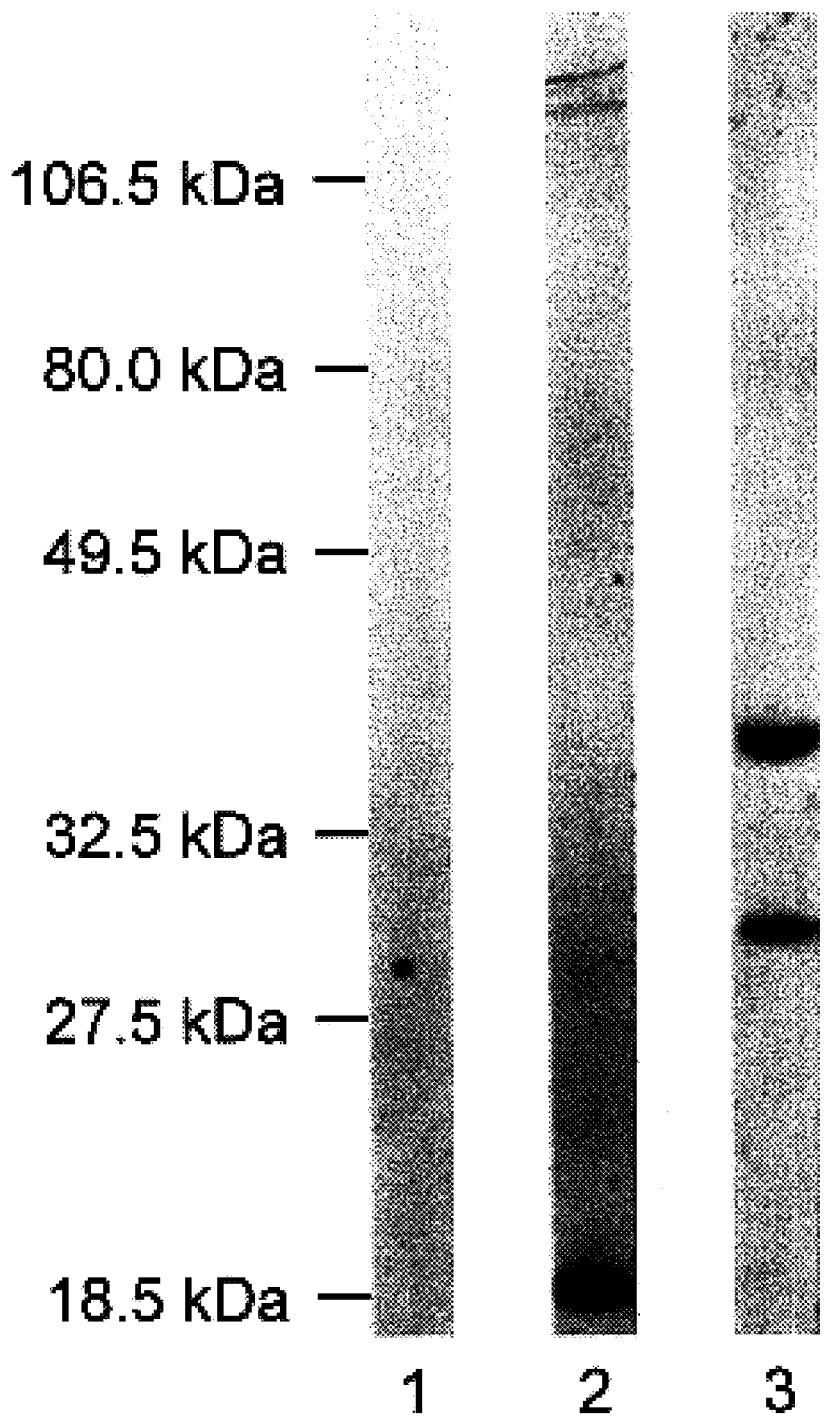
FIG. 11 depicts an immunoblot of *B. burgdorferi* extracts probed with mouse anti-GT (control) sera (lane 1), mouse anti-OspE sera (lane 2) or mouse anti-OspF sera (lane 3). All of the sera were diluted 1:5000.

We also used the antiserum from the immunized animals to confirm the identity of the cloned polypeptides. As shown in FIG. 11 (lane 2), antibodies from mice immunized with Δ20-OspE bound to a protein in *B. burgdorferi* extract which migrated at approximately 19 kDa. This size approximates the predicted size of the OspE protein of SEQ ID NO: 2 and thus could represent the processed, lipidated form of the OspE protein.

Mice immunized with Δ18-OspF detected two *B. burgdorferi* proteins (FIG. 11, lane 3). One migrated at approximately 29 kDa—the approximate size for a processed, lipidated OspF protein. The other protein migrated at approximately 36 kDa. Because the 36 kDa protein is immunologically cross-reactive with antibodies directed against an OspF polypeptide of this invention, it is, thus, also an OspF polypeptide of this invention.

The 36 kDa OspF polypeptide may be isolated by a variety of methods available to one of skill in the art. For example, anti-OspF antiserum could be used to screen the *B. burgdorferi* expression library constructed in Example I for clones capable of expressing that protein. Alternatively, an expression library could be constructed in which smaller fragments of *B. burgdorferi* DNA are cloned in frame into an expression vector from which they would be expressed as glutathione S-transferase rusion proteins, such as pGEX-2T, pMX, or pGEMEX. Such a library would have a high likelihood of expressing the sequence as a fusion protein, even if it is normally linked to a promoter that is not transcriptionally active in *E. coli*.

Figure 12A:
FIG. 12(A) depicts fixed *B. burgdorferi* spirochetes stained with rabbit antisera directed against Δ20-OspE.
Figure 12B:
FIG. 12(B) depicts fixed *B. burgdorferi* spirochetes stained with rabbit antisera directed against OspF.

Alternatively, the protein may be purified by immunoprecipitation, segments of the amino acid sequence determined, and oligonucleotides synthesized, which may then be used to screen-a genomic *B. burgdorferi* library We also used the rabbit anti-OspE and anti-OspF antisera in immunofluorescence studies to verify that OspE and OspF are expressed on the outer surface of the *B. burgdorferi* spirochete. Rabbit antisera directed against both Δ20-OspE and Δ18-OspF stained fixed *B. burgdorferi* N40, although at approximately only half the intensity as that achieved with antibodies directed against whole *B. burgdorferi* or recombinant OspA. FIG. 12(A) shows the staining pattern of spirochetes fixed with paraformaldehyde-and stained in suspension with rabbit anti-OspE sera diluted 1:100. FIG. 12(B) shows the staining pattern when anti-OspB diluted 1:100 is used. The staining pattern indicates that both the OspE and OspF proteins are exposed on the outer membrane of the spirochetes.

EXAMPLE VI

Characterization of the Immune Response to OspE and OspF

To further characterize the immune response to OspE and OspF during the course of infection, we infected normal mice intradermally with $10^4$ *B. burgdorferi* N40 and collected sera at day 30 and day 90 after infection. We then used this sera on Western blots of purified Δ20-OspE and Δ18-OspF polypeptides.

Figure 13:
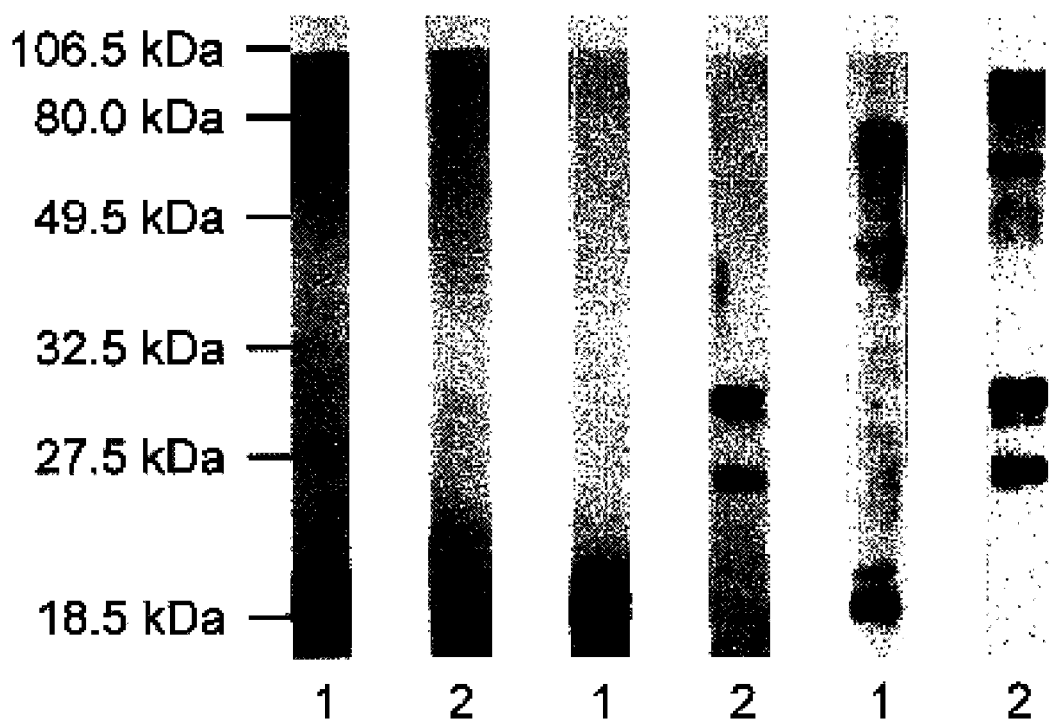
FIG. 13 depicts three pairs of immunoblots of Δ20-OspE and Δ18-OspF. The left-hand pair of lanes depicts immunoblots of Δ20-OspE (lane 1) and Δ18-OspF (lane 2) probed with sera taken from mice 30 days after infection with *B. burgdorferi*. The center pair of lanes depicts immunoblots of Δ20-OspE (lane 1) and Δ18-OspF (lane 2) probed with sera taken from mice 90 days after infection with *B. burgdorferi*. The right-hand pair of lanes depicts immunoblots of Δ20-OspE (lane 1) and Δ18-OspF (lane 2) probed with sera of a human patient with late-stage Lyme disease.

FIG. 13(a) shows that sera taken from mice 30 days after infection bound to Δ20-OspE (lane 1) but not to Δ18-OspF (lane 2). FIG. 13(b) shows that by 90 days after infection, anti-OspF antibodies were detectable, although at lower levels than those directed against OspE.

We also characterized the human immune response to the OspE and OspF proteins. We obtained sera from 28 patients with early stage Lyme disease (defined as patients having erythema migrans on the day of diagnosis and skin lesions for less than 1 week) and from 19 patients with late stage Lyme-disease (defined as patients having erythema migrans for at least six months).

As shown in Table I, below, 11% of the early stage Lyme disease patients had antibodies to OspE and 14% had antibodies to OspF. However, in the late stage patients, while only 15% had antibodies to OspE, 58% had antibodies to OspF.

TABLE I

| Stage of disease | No. of patients | Number (%) of patients with antibodies to | | |
|---|---|---|---|---|
| | | *B. burgdorferi* | OspE | OspF |
| Early | 28 | 26(93) | 3(11) | 4(14) |
| Late | 19 | 19(100) | 3(15) | 11(58) |

A representative immunoblot of the Δ20-OspE and Δ18-OspF polypeptides probed with human sera from a late-stage Lyme disease patient is shown in FIG. 13(c).

EXAMPLE VII

Ability of OspE and OspF to Protect Against *B. burgdorferi* Infection

To determine whether the OspE or OspF polypeptides were able to elicit an immune response that would be effective to protect against *B. burgdorferi* infection, we actively immunized C3H/He mice with the various OspE and OspF polypeptides described above, and then attempted to infect the immunized mice with *B. burgdorferi* N40.

We grew a low passage isolate of *B. burgdorferi* N40, with demonstrated infectivity and pathogenicity, to log phase in BSK II medium and counted with a hemocytometer under dark-field microscopy. We then challenged the actively immunized mice approximately 14 days after the last boost with intradermal inoculations of $10^2$ or $10^4$ spirochetes and sacrificed fourteen days after infection. We then cultured selected mouse tissues in BSK II medium to assay for spirochetes, and examined joints and hearts for inflammation.

As shown below in Table II, when mice immunized with either GT-OspF or Δ8-OspF were challenged intradermally with $10^2$ *B. burgdorferi*, they exhibited a low frequency of infection and disease in comparison to control mice ($P<0.05$ by $\chi^2$ test), indicating that OspF is capable of providing protection from *B. burgdorferi* infection. This protective effect was no longer apparent when the dose of spirochetes was increased to $10^4$.

However, that dose is likely to be considerably greater than that delivered by tick bite. In contrast, the mice immunized with GT-OspE or Δ20-OspE did not appear to be significantly protected from subsequent infection, regardless of the dose of *B. burgdorferi* administered.

TABLE II

| Challenge | Immununization (Active) | Culture[a] | Disease[b] | Infection[c] |
|---|---|---|---|---|
| $10^4$ N40 | OspE | 3/5 | 3/5 | 4/5 |
| | OspF | 3/5 | 2/5 | 3/5 |
| | Control | 3/5 | 2/5 | 3/5 |
| $10^2$ N40 | OspE | 4/9 | 2/9 | 4/9 |
| | OspF | 1/9 | 0/9 | 1/9 |
| | Control | 5/9 | 2/9 | 5/9 |

[a]A mouse was considered positive if spirochetes could be cultured from blood, spleen or bladder.
[b]Histological examination of joints and hearts.
[c]An animal was "infection" positive if it had a positive culture, evidence of disease, or both.

EXAMPLE VIII

Protection Against Tick-mediated Transmission

We also determined whether the protection conferred by immunization with OspF extended to tick-mediated transmission of the spirochete. We obtained spirochete-free Ixodes dammini ticks from the Harvard School of Public Health, which maintains a laboratory colony derived from an Ipswich, MA population. We infected the ticks (at the larval stage) by allowing them to feed to repletion on outbred CD-1 mice that had been previously infected (three weeks prior to serving as hosts) by intradermal inoculation of $10^3$ B. burgdorferi N40 spirochetes. Upon repletion, we collected engorged larvae, pooled them in groups of 100–200, and permitted them to molt to the nymphal stage at 21° C. and 95% relative humidity. We determined the prevalence of infection in each pool by immunofluorescence of a representative sample (10 ticks) three weeks after molting. We used only those pools having an infection prevalence of greater than 70% for challenge experiments.

We immunized mice with GT-OspE or Δ20-OspE and GT-OspF or Δ18-OspF or with BSA as a control, as described in Example V. Two weeks after the last boost, we placed 3 to 5 nymphal ticks on each mouse, allowed them to feed or repletion and then allowed them to detach naturaly over water. Two weeks later we sacrificed the mice in order to culture the tissues for spirochetes and examine the organs, as described above.

As shown below in Table III, the protective effect of immunization with OspF was again evident. In contrast, the frequency of B. burgdorferi infection in mice immunized with OspE appeared to be the same as in the control mice that had not been immunized.

TABLE III

| Immunization | Culture[a] | Disease[b] | Infection[c] |
|---|---|---|---|
| OspE | 6/12 | 5/12 | 7/12 |
| OspF | 2/12 | 2/12 | 2/12 |
| Control | 6/12 | 7/12 | 7/12 |

[a]A mouse was considered positive if spirochetes could be cultured from blood, spleen or bladder.
[b]Histological examination of joints and hearts.
[c]An animal was "infection" positive if it had a positive culture, evidence of disease, or both.

mice immunized with Δ20-OspE or 12 mice immunized with Δ18-OspF. After feeding to repletion, the ticks were allowed to naturally detached over water. Only a portion of the ticks were recovered from each group, the remainder apparently having been ingested by the mice. We homogenized individual ticks in 100 μl of PBS and spotted 10 μl aliquots on each of three slides. The slides were allowed to air-dry, fixed in cold acetone for 10 minutes, and assayed by direct or indirect immunofluorescence.

For the direct immunofluorescence assay, we stained with FITC-conjugated rabbit anti-B. burgdorferi serum at a dilution of 1:100. In the indirect immunofluorescence assay, we stained with the anti-OspA monoclonal antibody H5332 diluted 1:8 as a primary antibody, and FITC-conjugated goat anti-mouse IgG at a dilution of 1:100 as a secondary antibody. We quantified the spirochetes by counting the number of fluorescing cells in approximately 20 fields per slide.

As shown below in Table IV, while 85% of the ticks recovered from the control mice remained infected with spirochetes, only about 58% of the ticks that had fed on Δ20-OspE-immunized mice (P<0.05 by $c^2$ test), and 54% of the ticks that had fed on Δ18-OspF-immunized mice (P<0.01) remained infected. Moreover, the infected ticks that were recovered from the OspE- and OspF-immunized mice showed a much lower spirochete load than those that had fed on normal control mice. For example, while approximately 65% of the ticks that fed on control mice were found to carry more than 100 spirochetes/tick, that level of infection was maintained in only 17% of the ticks that had fed on OspE-immunized mice, and none of the ticks that had fed on OspF-immunized mice. Accordingly, while killing of spirochetes and protection against Lyme disease may not be absolute, we have shown that immunization with OspE polypeptides, and, to an even greater extent, OspF polypeptides, is able to prevent or lessen the severity of B. burgdorferi infection by effectively decreasing the spirochete load in infecting ticks.

TABLE IV

| | | | % infected ticks No. of spirochetes | | | | |
|---|---|---|---|---|---|---|---|
| Immunization | # Ticks examined | No. (%) infected | (1–3) | (3–50) | (50–100) | (≦500) | (>500) |
| OspE | 12 | 7 (58) | 8 | 25 | 8 | 17 | 0 |
| OspF | 24 | 13 (54) | 8 | 33 | 13 | 0 | 0 |
| Control | 20 | 17 (85) | 0 | 0 | 20 | 10 | 55 |

EXAMPLE IX

Decrease in Spirochete Load in Ticks Feeding on Immunized Animals

Previous studies have shown that immunization of mice with recombinant OspA can eliminate the spirochetes from ticks feeding on the immunized animals [E. Fikrig et al., "Elimination of Borrelia burgdorferi from vector ticks feeding on OspA-immunized mice", Proc. Natl. Acad. Sci., 89, pp. 5418–5421 (1992)]. Thus, we sought to determine if spirochetes would also be killed when infected ticks fed on animals immunized with OspE or OspF.

We placed five Ixodes dammini ticks, infected as described in Example VIII, on each of 12 control mice, 12

EXAMPLE X

Passive Immunization of Mice With Anti-OspF Antiserum

Because immunization with OspF polypeptides was able to confer protection against Lyme disease and B. burgdorferi infection, we sought to determine if passive immunization of mice with antiserum from OspF immunized animals would also confer protection. We passively immunized mice with 0.2 ml of sera from rabbits immunized with Δ18-OspF. We then challenged the passively immunized mice with $10^2$ B. burgdorferi N40 at one day after the immunization. Surprisingly, while immunization with OspF polypeptides is effective to prevent or lessen the severity of B. burgdorferi infection, the data shown below in Table V demonstrate that passive immunization with anti-OspF antiserum does not protect naive animals from subsequent infection.

TABLE V

| Challenge | Passive Immunization | Culture[a] | Disease[b] | Infection[c] |
|---|---|---|---|---|
| 10²N40 | anti-OspF antiserum | 8/15 | 3/15 | 8/15 |
|  | control | 7/15 | 2/15 | 7/15 |

[a]A mouse was considered positive if spirochetes could be cultured from blood, spleen or bladder.
[b]Histological examination or joints and hearts.
[c]An animal was "infection" positive if it had a positive culture, evidence of disease, or both.

EXAMPLE XI

Restriction Analysis of Additional Clones Comprising Novel *B. burgdorferi* Polypeptides As discussed in Example I, we had originally identified six clones from the *B. burgdorferi* expression library that did not hybridize with DNA probes to OspA, OspB or flagellin. In addition to clone #11, which contained the OspE-F operon, we had designated the remaining clones #4, #5, #7, #8, and #10. Restriction mapping of the clones indicated that clone #4 had a DNA insert of approximately 4.7 kb, clone #7 had a DNA insert of approximately 4.8 kb, clone #8 had a DNA insert of approximately 4.3 kb, and clone #10 had a DNA insert cf approximately 2.6 kb. We have not yet determined precisely the size of the DNA insert in clone #5.

EXAMPLE XI

Analysis of the *B. burgdorferi* T5 Protein

We excised the pBluescript plasmid from clone #10 as described in Example I. We then sequenced the DNA insert as described in Example II, after generating nested deletions using the Erase-A-Base System (with XhoI to generate the 5' blunt end and KpnI to generate the 3' overhang.)

The nucleotide sequence of the *B. burgdorferi* gene contained within clone #10 is shown in SEQ ID NO: 6.

The gene contains a 582-bp open reading frame capable of encoding a 194 amino acid protein (SEQ ID NO: 7) with a predicted molecular weight of 21.8 kd. We designated this protein the "T5" protein. As for the OspE and OspF genes, the gene encoding T5 contains a ribosomal binding site similar to the Shine-Dalgarno sequence and −10 and −35 promoter regions similar to those found in *E. coli* and other *B. burgdorferi* genes.

Figure 14:
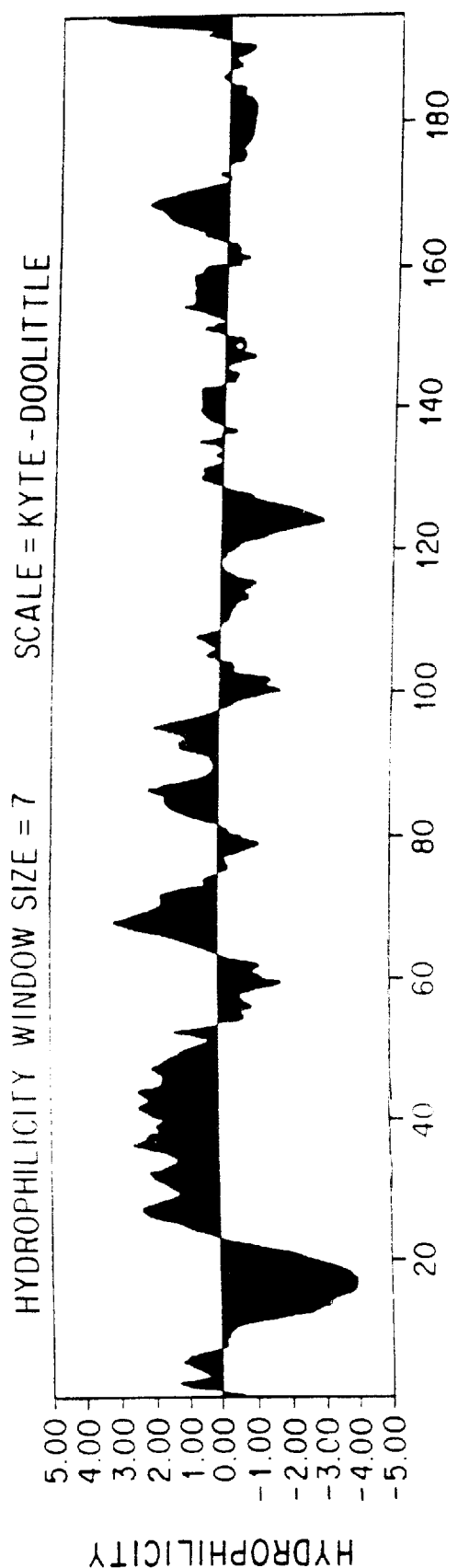
FIG. 14 depicts the hydrophilicity profile of the T5 protein.

The hydrophilicity profile (FIG. 14) and deduced amino acid sequence of T5 (SEQ ID NO: 7) reveal a leader peptide similar to those found in typical prokaryotic lipoprotein precursors. The leader signal sequence begins with a short positively charged peptide at the amino terminus, followed by a hydrophobic domain of 16 amino acids. At the carboxy terminus of the hydrophobic core is a signal peptidase II cleavage site that is similar to that of the OspE and OspF genes (amino acid 18–22 of SEQ ID NO: 7) The lipoprotein processing site is followed by a stretch of about 30 hydrophilic amino acids. Beyond that domain, the hydrophilicity plot shows mixed intervals of hydrophobic and hydrophilic regions.

EXAMPLE XII

Expression and Purification of T5

Figure 15:
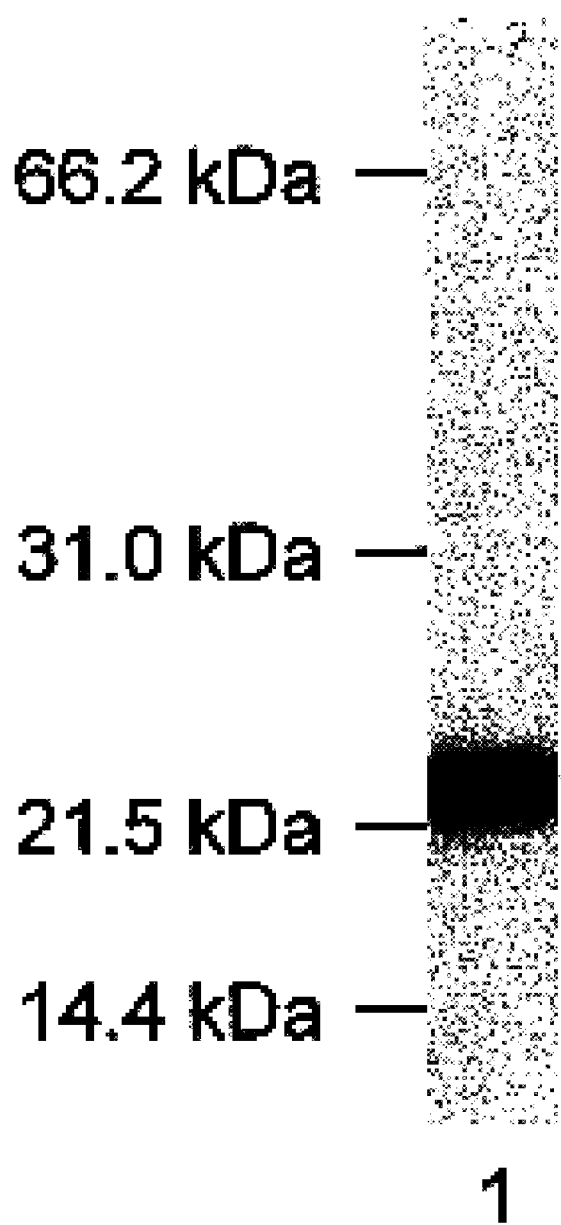
FIG. 15 depicts a coomasie-stained SDS-PAGE gel of the cleaved T5 protein.

We amplified the T5 DNA sequence lacking the portion coding for the leader peptide which contains the lipidation signal sequence, cloned the insert into pMX, expressed the protein as a glutathione S-transferase fusion protein, and cleaved the *B. burgdorferi* T5 protein sequences as described for the OspE and OspF proteins in Example IV. We then electrophoresed the cleaved protein on an SDS-PAGE gel. As shown in FIG. 15, the cleaved protein migrated at an apparent molecular weight of 22 kDa.

EXAMPLE XIII

Chromosomal Mapping of the T5 Gene

Figure 16:
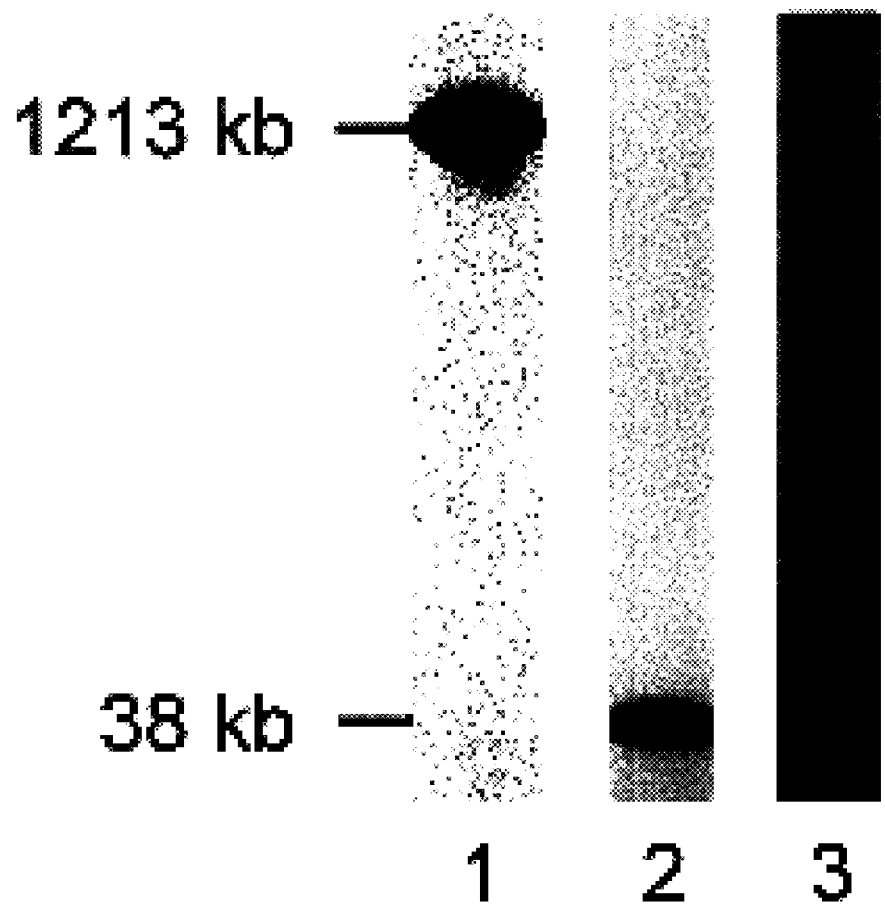
FIG. 16 Southern blots of several lanes of *B. burgdorferi* DNA separated by pulsed-field gel electrophoresis and hybridized with various *B. burgdorferi* probes. Lane 1 is hybridized with a flagellin probe, lane 2 with an OspD probe, lane 3 with a T5 probe.

We performed pulsed-field electrophoresis as described in Example III, blotted the gel, and hybridized with various *B. burgdorferi* probes. As shown in FIG. 16 (lane 3), the T5 probe hybridized to the *B. burgdorferi* band corresponding to the linear chromosome. Accordingly, unlike the other outer surface proteins identified to date, it appears that the T5 protein is not encoded by a plasmid of *B. burgdorferi*. This could suggest that the T5 protein may be more conserved among various *B. burgdorferi* isolates than the plasmid-encoded outer surface proteins.

Given the DNA sequence encoding the T5 protein, one of skill in the art can easily determine the degree of variability of this protein across various *B. burgdorferi* strains, either by producing antibodies against the protein and determining the extent of cross-reactivity, or by using the DNA as a probe for hybridization to the DNA of different *B. burgdorferi* isolates. The various isolates would then be sequenced to determine the precise differences.

EXAMPLE XIV

Sequence Analysis of the *B. burgdorferi* S1 Protein

We also determined the sequence of the *B. burgdorferi* DNA contained within clone #8. That DNA sequence is shown in SEQ ID NO: 4. The DNA contains an open reading frame of 1251 base pairs, capable of encoding a protein of 417 amino acids (SEQ ID NO: 5) with a predicted molecular weight of 48.9 kDa. We designated this protein the "S1" protein. As for OspE and OspF the gene encoding S1 contains a ribosomal binding site similar to the Shine-Dalgarno sequence and −10 and −35 promoter regions similar to those found in *E. coli* and other *B. burgdorferi* genes.

The hydrophilicity profile (data not shown) and deduced amino acid sequence of S1 reveal a leader peptide similar to those found in typical prokaryotic lipoprotein precursors. The leader signal sequence consists of a hydrophobic domain of 18 amino acids. At the carboxyl terminus of the hydrophobic core is a signal peptidase II cleavage site that is similar to that of the OspE and OspF genes (amino acid 14–18 of SEQ ID NO: 5).

EXAMPLE XV

Analysis of Additional Novel *B. burgdorferi* Polypeptides

We excise the pBluescript plasmids from clones #4, #5 and #7 as described above. We then sequence the clones and insert the sequences, in whole or in part, into expression vectors in order to express novel *B. burgdorferi* polypeptides. We then use each of the novel *B. burgdorferi* polypeptides of this invention to immunize rabbits or C3H/He mice and demonstrate the ability of the polypeptides to prevent or lessen the severity, for some period of time, of *B. burgdorferi* infection.

EXAMPLE XVI

Determination of Protective Epitopes

We construct recombinant genes which will express fragments of the novel *B. burgdorferi* polypeptides in order to determine which fragments contain protective epitopes. First, we produce overlapping 200–300 bp fragments which encompass the entire nucleotide sequence of each of the genes, either by restriction enzyme digestion, or by amplification of specific sequences of using PCR and oligonucleotide primers containing restriction endonuclease recognition'sequences, as described supra. We then clone these fragments into an appropriate expression vector, preferably a vector from which the fragments will be expressed as fusion proteins, in order to facilitate purification and increase stability. For example, the gene fragments could be cloned into pGEMEX (Promega, Madison, Wis.) and expressed as T7 gene 10 fusion proteins. Such proteins would be insoluble and thus easily purified by recovery of the insoluble pellet fraction followed by solubilization in denaturants such as urea. Alternatively, the fragments could be expressed as glutathione S-transferase fusion proteins as described above. We then transform appropriate host cells and induce expression of the fragments.

One way to identify fragments that contain protective B-cell epitopes is to use the individual purified fragments to immunize C3H/HeJ mice, as described above. After challenge of the nice with *B. burgdorferi*, we determine the presence of infection by blood and spleen cultures and by histopathologic examination of the joints and heart.

Another technique to identify protective epitopes is to use the various fragments to immunize mice, allow ticks infected with *B. burgdorferi* to feed on the mice, and then determine, as set forth in Example VIII, whether the immune response elicited by the fragments is sufficient to cause a decrease in the level of *B. burgdorferi* in the ticks. Any epitopes which elicit such a response, even if they are not sufficient by themselves to confer protection against subsequent infection with *B. burgdorferi*, may be useful in a multicomponent vaccine.

Once we have localized various epitopes to particular regions of the fusion proteins, we conduct further analyses using short synthetic peptides of 5–35 amino acids. The use of synthetic peptides allows us to further define each epitope, while eliminating any variables contributed by the non-*B. burgdorferi* portion of the fusion protein.

EXAMPLE XVII

Preparation of a Multicomponent Vaccine

We determine which of the protective epitopes is able to elicit antibodies that will protect against subsequent infection with strains of *B. burgdorferi* other than the strain from which the Osp gene was cloned. We then design a vaccine around those epitopes. If none of the protective epitopes is able to confer protection against infection with other strains of *B. burgdorferi*, it may be particularly advantageous to isolate the corresponding novel *B. burgdorferi* polypeptides from those strains. A multicomponent vaccine may then be constructed that comprises multiple epitopes from several different *B. burgdorferi* isolates. Such a vaccine will, thus, elicit antibodies that will confer protection against a variety of different strains.

EXAMPLE XVIII

Identification of T Cell Epitopes

Stimulation in animals of a humoral immune response containing high titer neutralizing antibodies will be facilitated by antigens containing both T cell and B cell epitopes. To identify those polypeptides containing T cell epitopes, we infect C3H/HeJ mice with *B. burgdorferi* strain N40 in complete Freund's adjuvant, as described supra. Ten days after priming, we harvest the lymph nodes and generate in vitro T cell lines. These T cell lines are then cloned using limiting dilution and soft agar techniques. We use these T cell clones to determine which polypeptides contain T cell epitopes. The T cell clones are stimulated with the various polypeptides and syngeneic antigen presenting cells. Exposure of the T cell clones to the polypeptides that contain T cell epitopes in the presence of antigen presenting cells causes the T cells to proliferate, which we measure by $^3$H-Thymidine incorporation. We also measure lymphokine production by the stimulated T cell clones by standard methods.

To determine T cell epitopes of the polypeptides recognized by human T cells, we isolate T cell clones from *B. burgdorferi*-infected patients of multiple HLA types. T cell epitopes are identified by stimulating the clones with the various polypeptides and measuring $^3$H-Thymidine incorporation. The various T cell epitopes are then correlated with Class II HLA antigens such as DR, DP, and DQ. The correlation is performed by utilization of B lymphoblastoid cell lines expressing various HLA genes. When a given T cell clone is mixed with the appropriate B lymphoblastoid cell line and a novel *B. burgdorferi* polypeptide, the B cell will be able to present the polypeptide to the T cell. Proliferation is then measured by $^3$H-Thymidine incorporation.

Alternatively, T cell epitopes may be identified by adoptive transfer of T cells from mice immunized with various of the novel *B. burgdorferi* polypeptides of this invention to naive mice, according to methods well known to those of skill in the art. [See, for example, M. S. DeSouza et al., "Long-Term Study of Cell-Mediated Responses to *Borrelia burgdorferi* in the Laboratory Mouse", *Infect. Immun.*, 61, pp. 1814–22 (1993)].

We then synthesize a multicomponent vaccine based on different T cell epitopes. Such a vaccine is useful to elicit T cell responses in a broad spectrum of patients with different HLA types.

We also identify stimulating T cell epitopes in other immunogenic *B. burgdorferi* polypeptides or in non-*B. burgdorferi* polypeptides and design multicomponent vaccines based on these epitopes in conjunction with B cell and T cell epitopes from the novel *B. burgdorferi* polypeptides of this invention.

EXAMPLE XIX

Construction of Fusion Proteins Comprising T and B cell Epitopes

After identifying T cell epitopes of the novel *B. burgdorferi* polypeptides, we construct recombinant proteins comprising these epitopes as well as the B cell epitopes recognized by neutralizing antibodies. These fusion proteins, by virtue of containing both T cell and B cell epitopes, permit antigen presentation to T cells by B cells expressing surface immunoglobulin. These-T cells in turn stimulate B cells that express surface immunoglobin, leading to the production of high titer neutralizing antibodies.

We also construct fusion proteins from the novel *B. burgdorferi* polypeptides by linking regions of the polypeptides determined to contain B cell epitopes to strong T cell epitopes of other antigens. We synthesize an oligonucleotide homologous to amino acids 120 to 140 of the Hepatitis B virus core antigen. This region of the core antigen has been shown to contain a strong T cell epitope [D. R. Millich, et al., supra]. The oligonucleotide is then ligated to the 5' and 3' ends of segments of DNA encoding the B cell epitopes recognized by neutralizing antibodies, as in Example XI. The recombinant DNA molecules are then used to express a fusion protein comprising a B cell epitope from the novel *B. burgdorferi* polypeptide and a T cell epitope from the core antigen, thus enhancing the immunogenicity of the polypeptide.

We also construct fusion proteins comprising epitopes of the novel *B. burgdorferi* polypeptides as well as epitopes of the tetanus toxoid protein.

We also construct a plasmid containing the B cell epitopes of various of the novel *B. burgdorferi* polypeptides incorporated into the flagellin protein of Salmonella. Bacterial flagellin are potent stimulators of cellular and humoral responses, and can be used as vectors for protective antigens [S. M. C. Newton, C. Jacob, B. Stocker, "Immune Response To Cholera Toxin Epitope Inserted In Salmonella Flagellin", *Science*, 244, pp. 70–72 (1989)]. We cleave the cloned H 1-d flagellin gene of *Salmonella muenchens* at a unique Eco RV site in the hypervariable region. We then insert blunt ended DNAs encoding protective B cell epitopes of the polypeptides using T4 DNA ligase. The recombinant plasmids are then used to transform non-flagellate strains of Salmonella for use as a vaccine. Mice are immunized with live and formalin killed bacteria and assayed for antibody production. In addition spleen cells are tested for proliferative cellular responses to the peptide of interest. Finally the mice immunized with this agent are challenged with *B. burgdorferi* as described supra.

We also construct fusion proteins comprising B cell epitopes from one of the novel *B. burgdorferi* polypeptides and T cell epitopes from a different novel *B. burgdorferi* polypeptide or other immunogenic *B. burgdorferi* polypeptides. Additionally, we construct fusion proteins comprising T cell epitopes from novel *B. burgdorferi* polypeptides and B cell epitopes from a novel *B. burgdorferi* polypeptide and/or other immunogenic *B. burgdorferi* polypeptides. Construction of these fusion proteins is accomplished by recombinant DNA techniques well known to those of skill in the art. Fusion proteins and antibodies directed against them, are used in methods and composition to detect, treat, and prevent Lyme disease as caused by infection with *B. burgdorferi*.

While we have described a number of embodiments of this invention, it is apparent that our basic constructions may be altered to provide other embodiments which utilize the processes and products of this invention. Therefore, it will be appreciated that the scope of this invention is to be defined by the appended claims, rather than by the specific embodiments which have been presented by way of example.

We claim:

1. An isolated antibody that binds to a *B. burgdorferi* polypeptide selected from the group consisting of:
    (a) an OspE polypeptide of SEQ ID NO: 2;
    (b) an S1 polypeptide of SEQ ID NO: 5;
    (c) an immunogenic fragment comprising at least 8 amino acids taken as a block from any one of the polypeptides of (a)–(b).

2. An isolated antibody that binds to a *B. burgdorferi* polypeptide selected from the group consisting of:
    (a) an OspF polypeptide of SEQ ID NO: 3; and
    (b) a fragment of the OspF polypeptide of SEQ ID NO: 3 from amino acid 19–230.

3. A diagnostic kit comprising an antibody according to claim 1 or claim 2.

4. A method for detecting *B. burgdorferi* infection comprising the steps of:
    (a) contacting a body fluid of a mammalian host with an antibody according to claim 1 or claim 2; and
    (b) detecting binding of said antibody to *B. burgdorferi* or said polypeptide.

5. An antibody according to claim 1 or 2, wherein the antibody is monoclonal.

6. A diagnostic kit comprising an antibody according to claim 5.

7. A method for detecting *B. burgdorferi* infection comprising the steps of
    (a) contacting a body fluid of a mammalian host with an antibody according to claim 5; and
    (b) detecting binding of said antibody to *B. burgdorferi* or said polypetide.

* * * * *